(12) United States Patent
Ventura

(10) Patent No.: US 11,574,729 B1
(45) Date of Patent: Feb. 7, 2023

(54) AUTOMATED DECISION SUPPORT COMPUTER SYSTEM FOR INFORMATICS CLASSIFICATION AND EVALUATION

(71) Applicant: Gustavo M. Ventura, Washington, DC (US)

(72) Inventor: Gustavo M. Ventura, Washington, DC (US)

( * ) Notice: Subject to any disclaimer, the term of this patent is extended or adjusted under 35 U.S.C. 154(b) by 0 days.

(21) Appl. No.: 16/112,013

(22) Filed: Aug. 24, 2018

Related U.S. Application Data

(60) Provisional application No. 62/550,370, filed on Aug. 25, 2017.

(51) Int. Cl.
G16H 40/20 (2018.01)
G16H 10/60 (2018.01)

(52) U.S. Cl.
CPC ............ *G16H 40/20* (2018.01); *G16H 10/60* (2018.01)

(58) Field of Classification Search
CPC .......... G06N 20/00; G06N 3/02; G06N 5/046; G06N 7/005; G06N 3/0472; G16H 40/40; G16H 10/60; G16H 40/00; G16H 50/20; G16H 50/50; G16H 50/70; G16H 80/00
See application file for complete search history.

(56) References Cited

U.S. PATENT DOCUMENTS

| | | | | |
|---|---|---|---|---|
| 2014/0233412 A1* | 8/2014 | Mishra | ............... | H04W 84/02 370/252 |
| 2015/0019470 A1* | 1/2015 | Park | ............... | G06N 5/048 706/47 |
| 2015/0254564 A1* | 9/2015 | Rodriguez | ............... | G06N 5/04 706/52 |
| 2018/0314798 A1* | 11/2018 | Hernandez | ............... | G16H 50/20 |

FOREIGN PATENT DOCUMENTS

CA  2654679 A1 *  8/2009  ............. G06Q 50/24

OTHER PUBLICATIONS

Agca,Esra.Optimization-Based LogisticsPlanningandPerformance MeasurementforHospitalEvacuationandEmergency Management. Diss.VirginiaTech,2013 (Year: 2013).*

(Continued)

*Primary Examiner* — Linh Giang Le
*Assistant Examiner* — Constantine B Siozopoulos
(74) *Attorney, Agent, or Firm* — Banner & Witcoff, Ltd.

(57) ABSTRACT

An automated decision support computer system based on data informatics, includes a first computer readable processing component including a plurality of resource attribute data profiles in which the resource attribute data profiles are generated at least partly from a plurality of electronic computer readable destination records. A second computer readable processing component includes a plurality of patient classification attribute data profiles in which the patient classification attribute data profiles are generated at least partly from a plurality of computer readable electronic health records. The automated decision support computer system also includes a decision support classification computer engine for scoring and ranking the plurality of resource attribute data profiles with the plurality of patient classification attribute data profiles to generate a computer readable evaluation attribute data profile for display on a computer screen.

15 Claims, 31 Drawing Sheets

(56) References Cited

OTHER PUBLICATIONS

Taaffe, Kevin, Matt Johnson, and Desiree Steinmann. "Improving hospital evacuation planning using simulation." Proceedings of the 2006 Winter Simulation Conference. IEEE, 2006. (Year: 2006).*
Sung, Inkyung, and Taesik Lee. "Optimal allocation of emergency medical resources in a mass casualty incident: Patient prioritization by column generation." European Journal of Operational Research 252.2 (2016): 623-634. (Year: 2016).*

\* cited by examiner

Figure 13

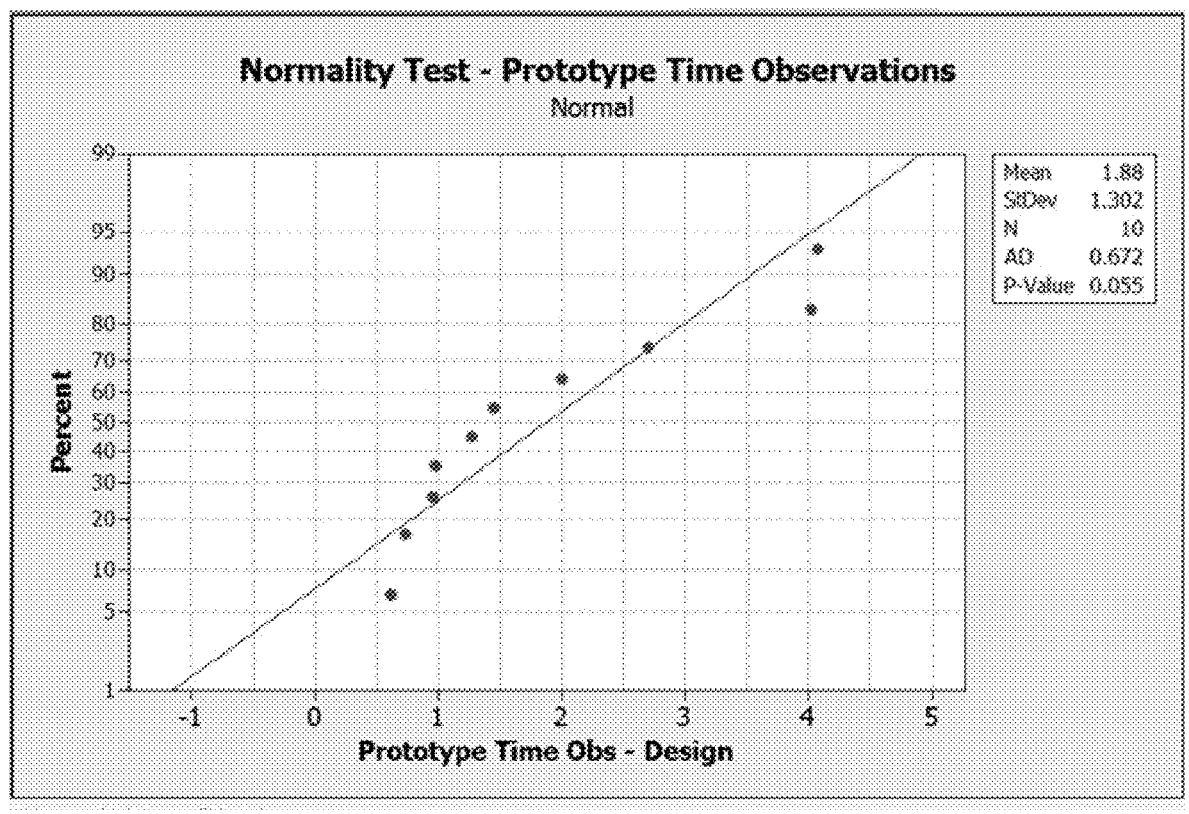
Figure 14  Normality Test - *Prototype Time Observations*
$p(0.055) > \alpha(0.05), but < \alpha(0.1)$

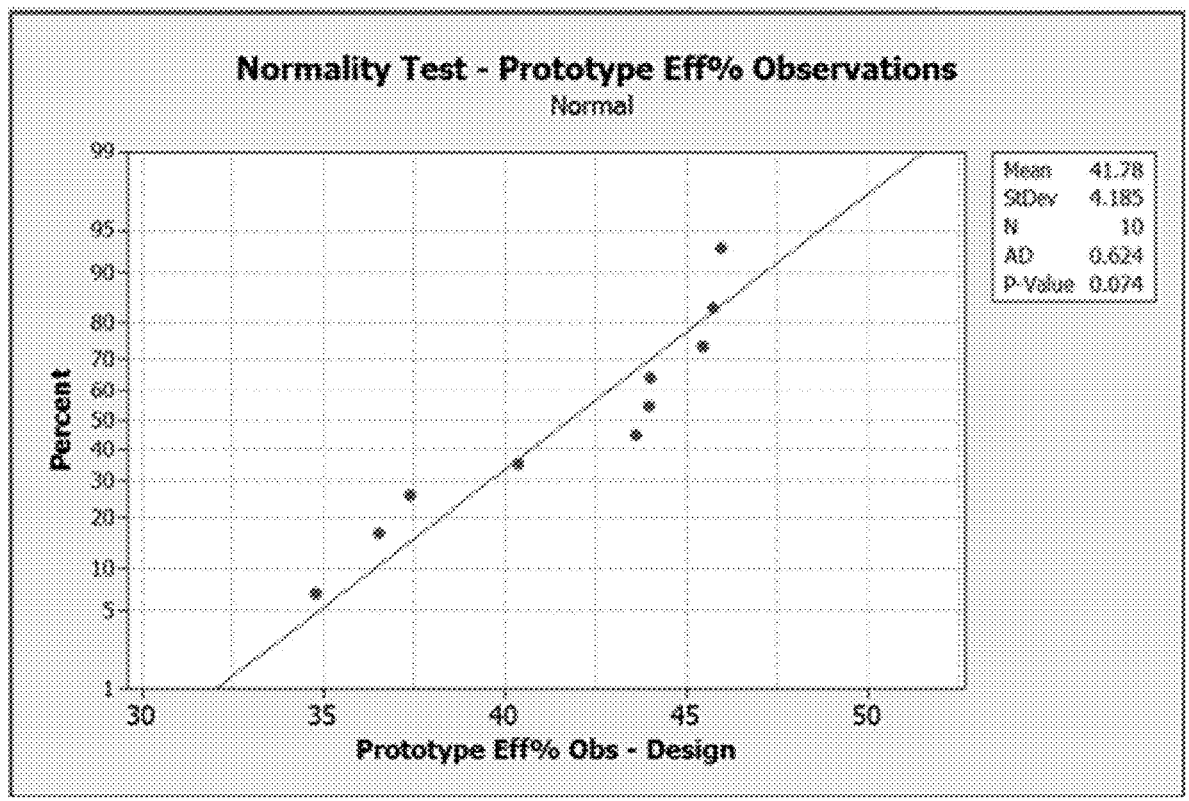
Figure 15 Normality Test - Prototype Efficiency Observations
$p(0.074) > \alpha(0.05), \text{but} < \alpha(0.10)$

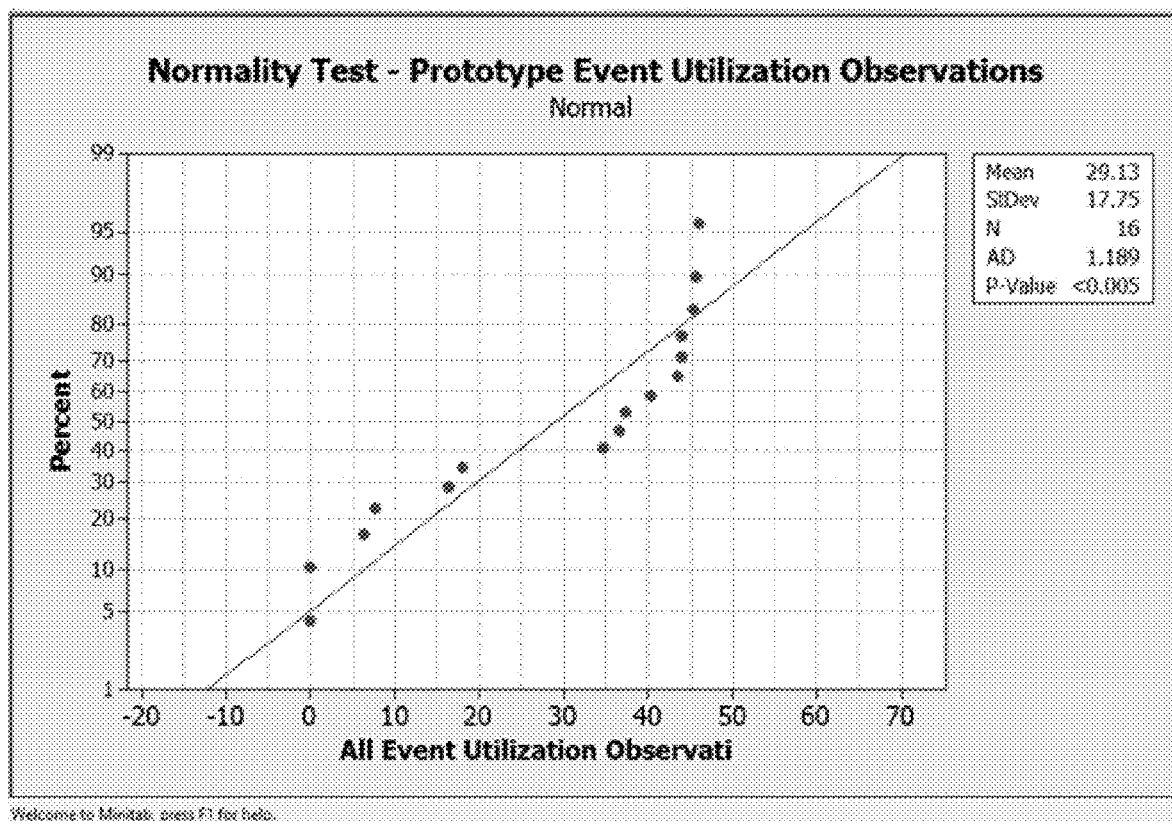
Figure 16  Normality Test – Event Utilization Observations
$p(0.005) < \alpha(0.05)$

```
General Linear Model: All Event Utiliz versus Treatment - Patient Files

Factor                        Type   Levels  Values
Treatment - Patient Files     fixed       2  A, B Analysis of Variance for All Event Utilization Observati, using Adjusted SS for
     Tests Source                       DF   Seq SS   Adj SS   Adj MS      F      P
Treatment - Patient Files     1    157.4    157.4    157.4   0.48  0.499
Error                        14   4567.7   4567.7    326.3
```

Figure 17  Normality Test – Event Utilization Residuals (Patient Files)
$p(0.499) > \alpha(0.05), and\ \alpha(0.1)$

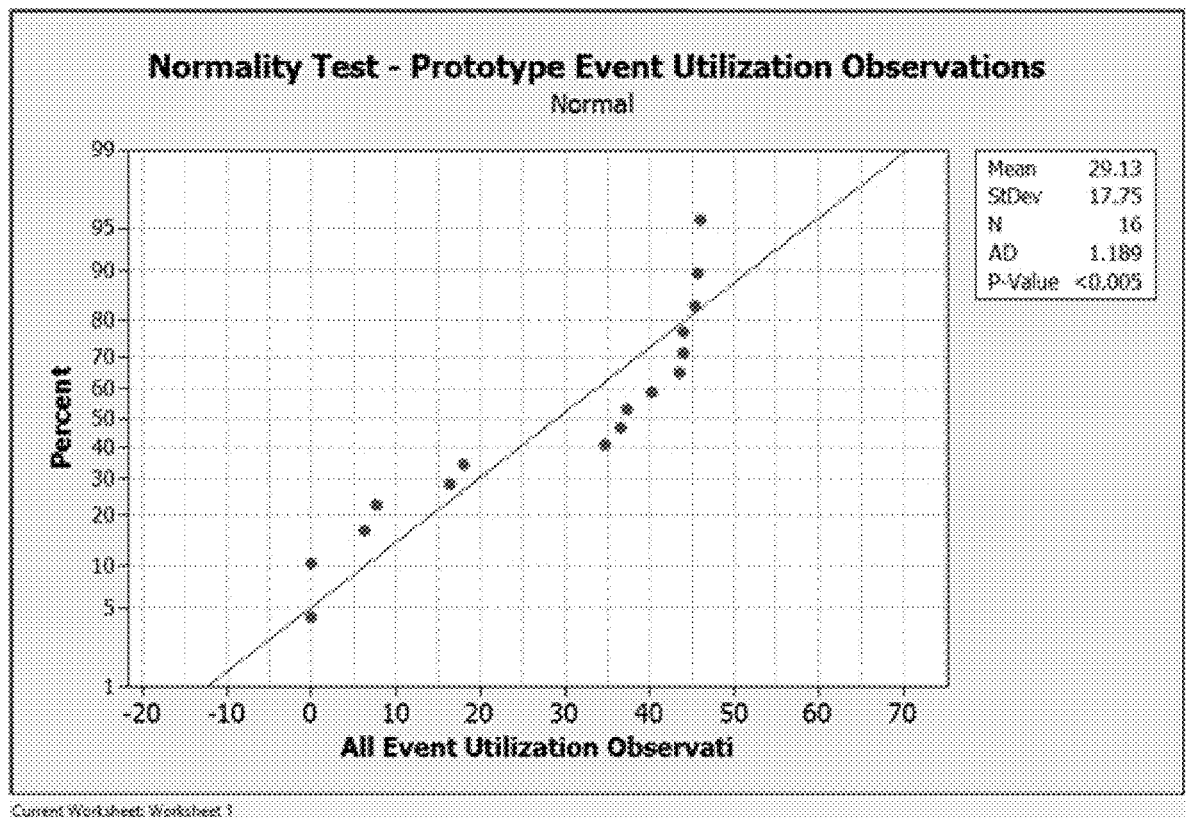
Figure 18  Normality Test – Residuals for *Event Utilization Observations* and associated *Patient Files*
$p(0.005) < \alpha(0.05)$

```
General Linear Model: All Event Utiliz versus Treatment - Group Assignment

Factor                          Type   Levels  Values
Treatment - Group Assignment    fixed       4  G1, G2, G3, G4

Analysis of Variance for All Event Utilization Observati, using Adjusted SS for
    Tests Source                          DF  Seq SS  Adj SS  Adj MS    F      P
Treatment - Group Assignment     3   922.0   922.0   307.3  0.97  0.439
Error                           12  3803.1  3803.1   316.9
```

Figure 19   Normality Test – Event Utilization Observations Residuals
(Group Assignments)
$p(0.439) > \alpha(0.05), and\ \alpha(0.1)$

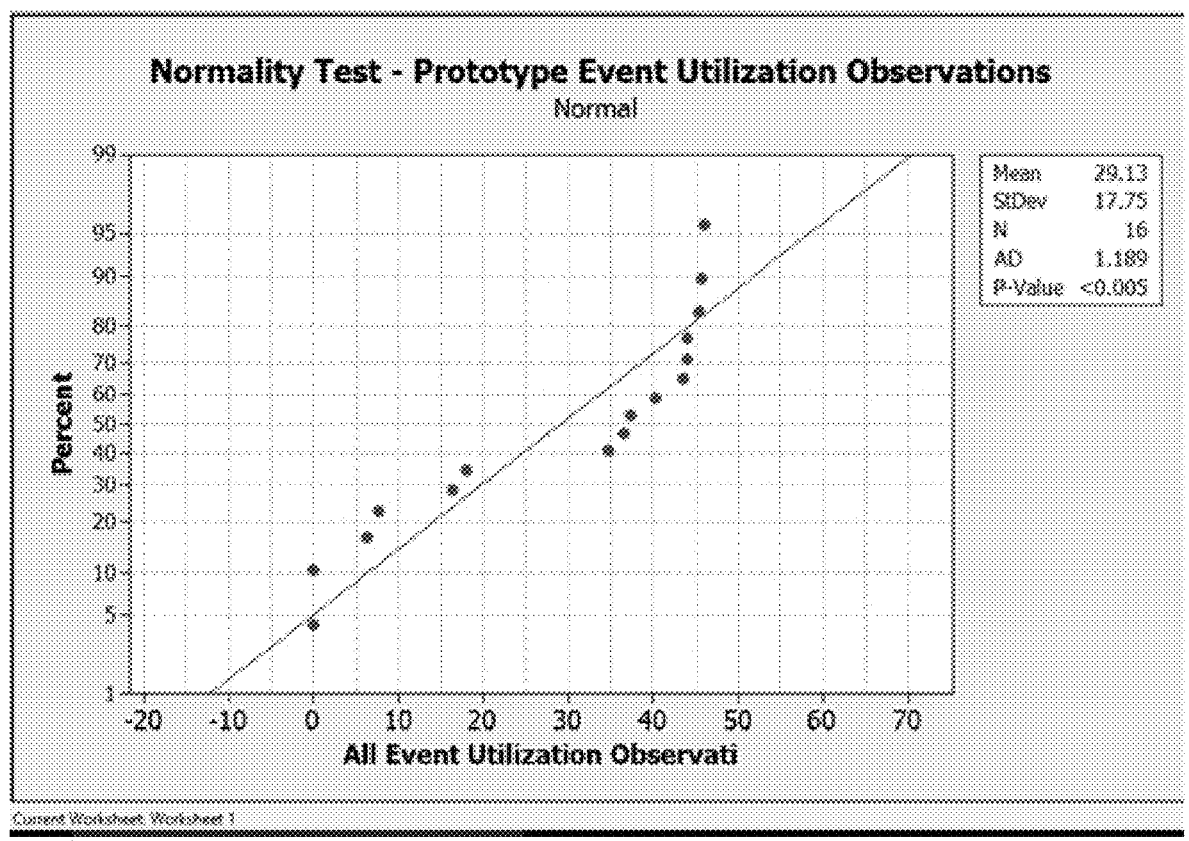
Figure 20  Normality Test – Residuals for *Event Utilization Observations* and associated *Group Assignment*
$$p(0.005) < \alpha(0.05)$$

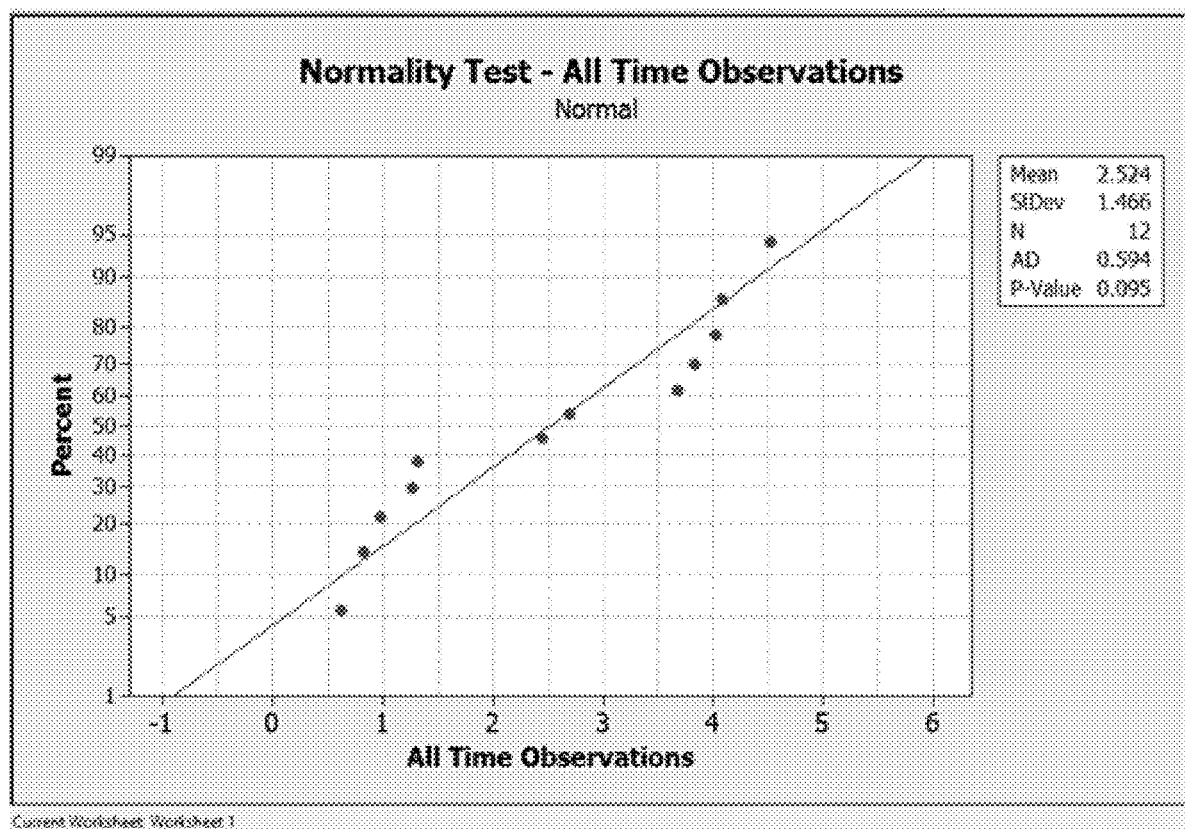
Figure 21    Normality Test - Time Observations
(Groups 1 and 2)
$p(0.095) > \alpha(0.05), but < \alpha(0.1)$

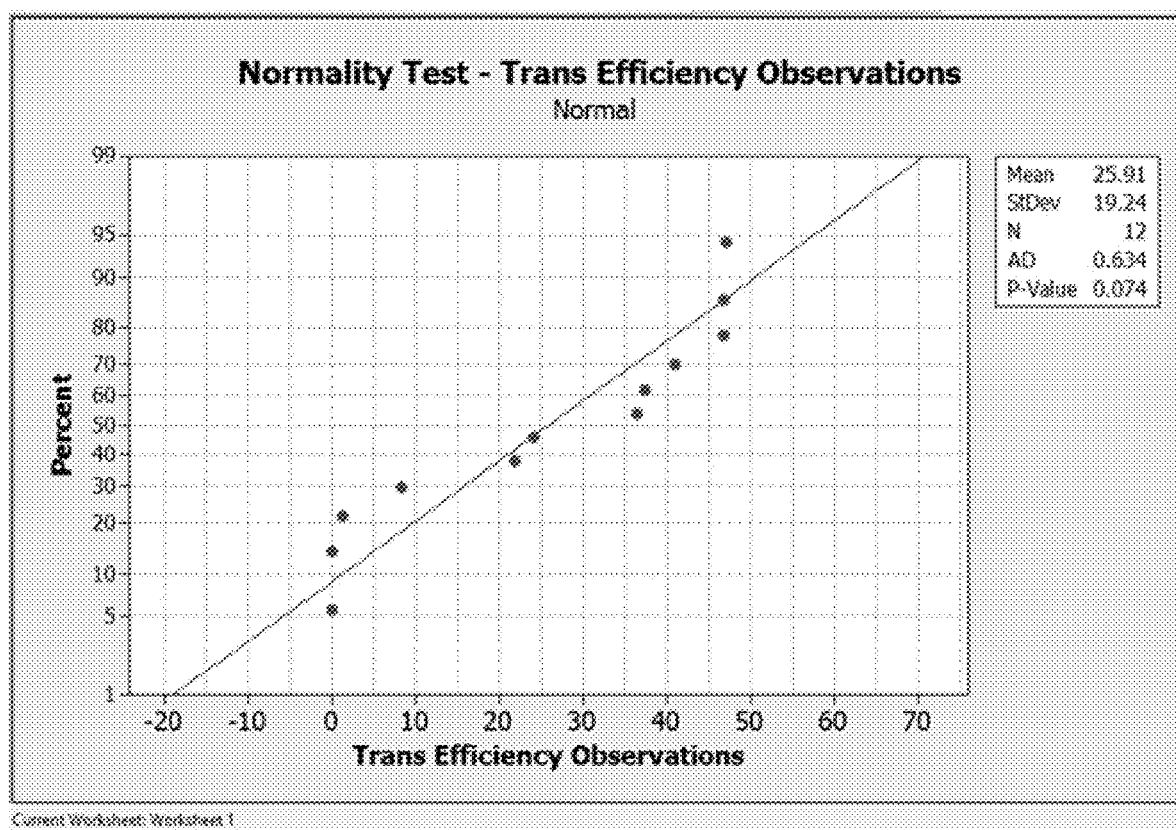
Figure 22  Normality Test – Transportation Efficiency Observations
(Groups 1 and 2)
$p(0.074) > \alpha(0.05), but < \alpha(0.1)$

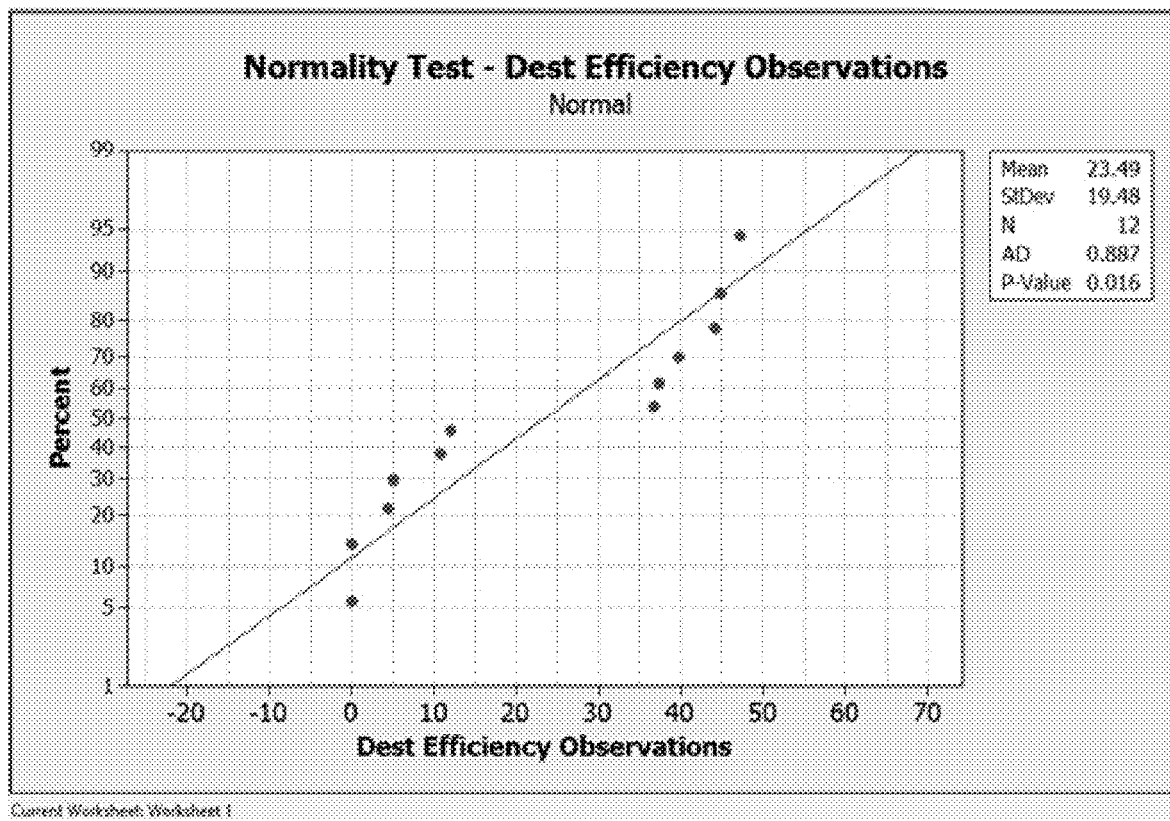
Figure 23   Normality Test – Destination Efficiency Observations
(Groups 1 and 2)
$p(0.016) < \alpha(0.05), and\ \alpha(0.1)$

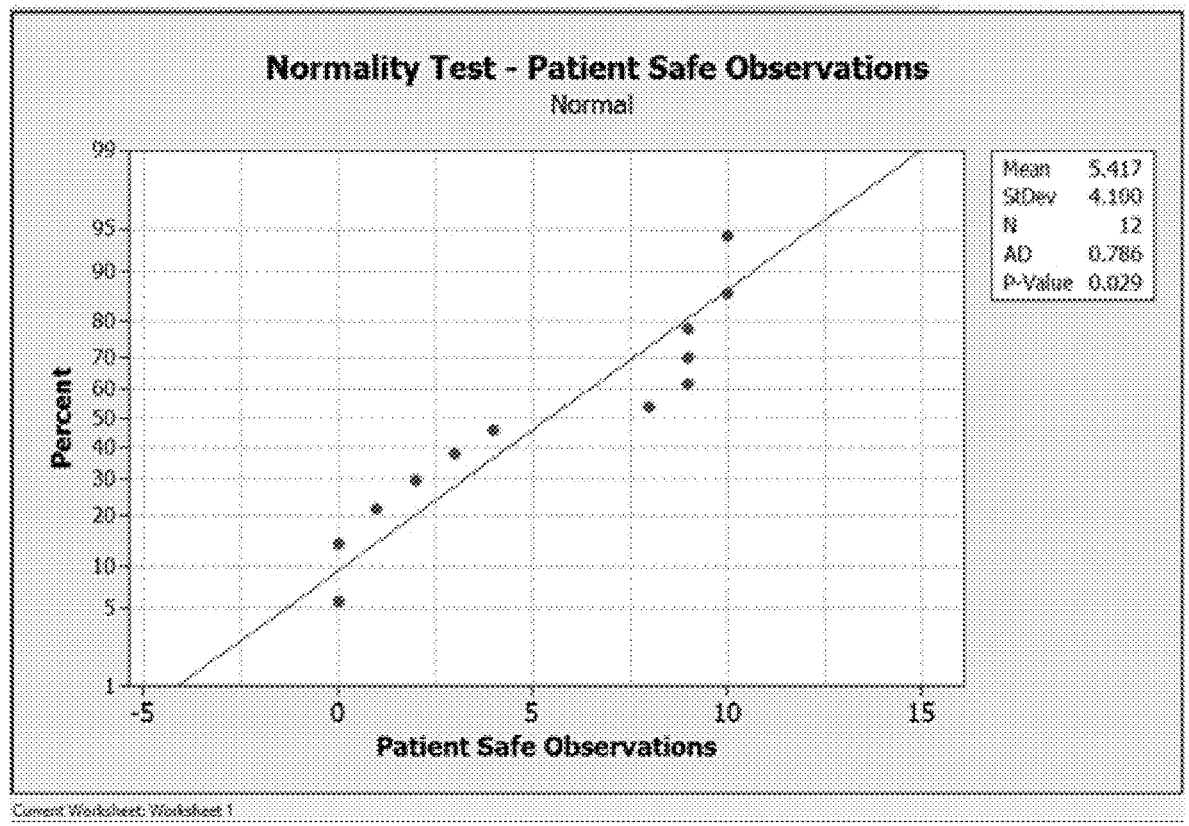
Figure 24  Normality Test – Patient Safety Observations
(Groups 1 and 2)
$p(0.029) < \alpha(0.05), and\ \alpha(0.1)$

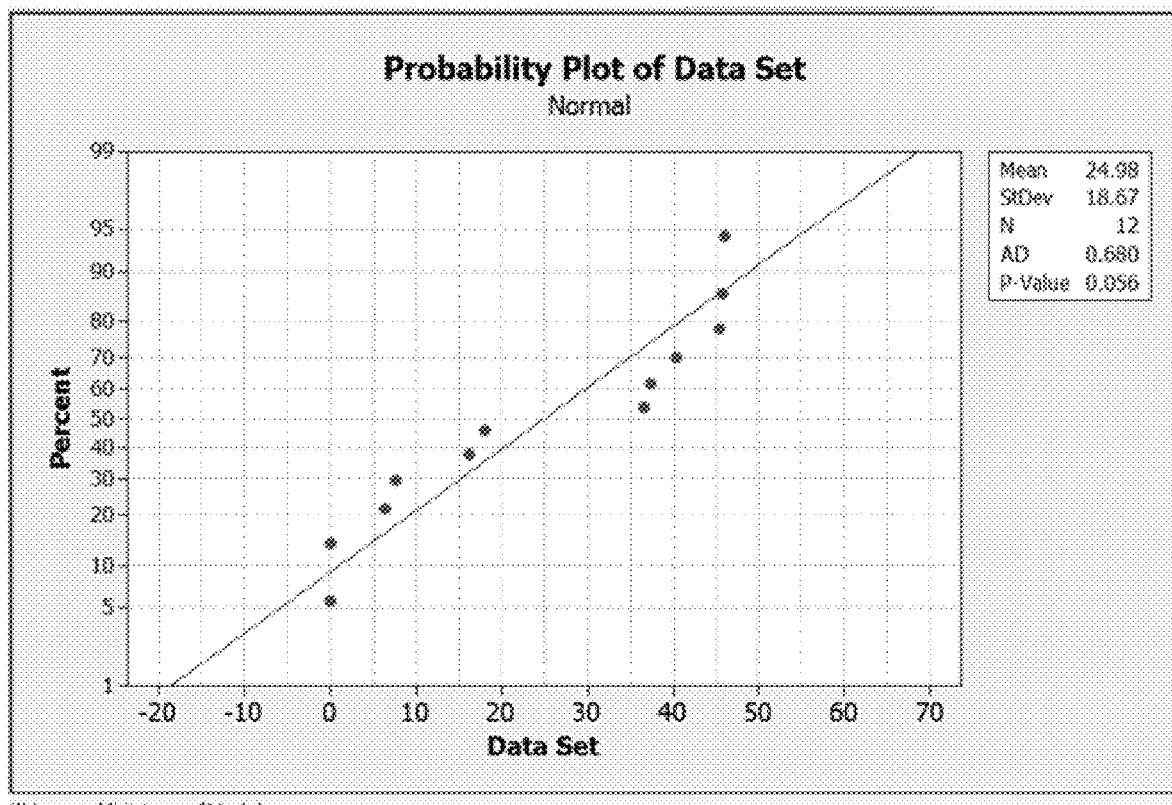
Figure 25 Normality Test – Event Utilization
(Groups 1 and 2)
$p(0.056) > \alpha\ (0.05), but < \alpha(0.1)$

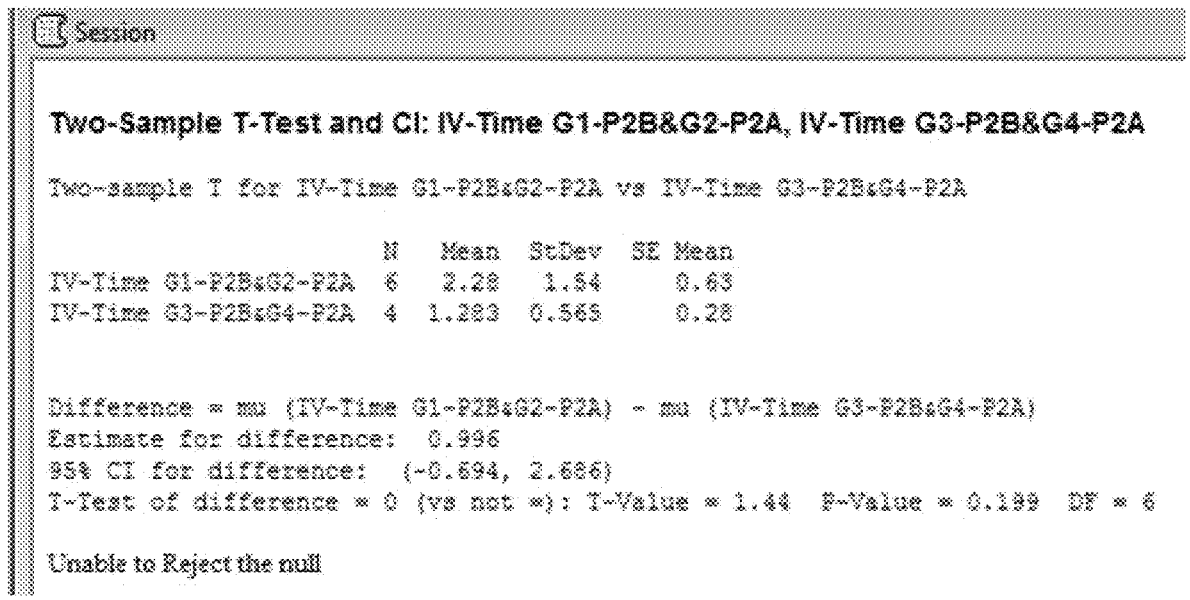
Figure 26  Data Element Test – Prototype Time Observations
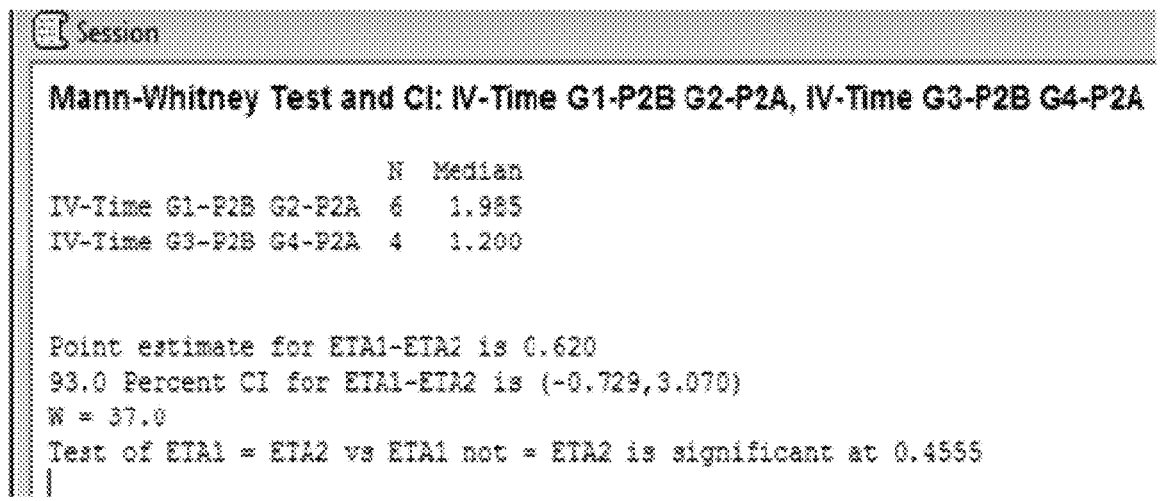
Figure 27  Data Element Test – Prototype Time Observations

```
Two-Sample T-Test and CI: IV - Eff G1 and G2 - Aft, IV - Eff G3 and G4 - Aft Two-sample T for IV - Eff G1 and G2 - After vs IV - Eff G3 and G4 - After N    Mean   StDev  SE Mean
IV - Eff G1 and G2 - Aft      6   43.00    3.80     1.5
IV - Eff G3 and G4 - Aft      4   39.95    4.59     2.3

Difference = mu (IV - Eff G1 and G2 - After) - mu (IV - Eff G3 and G4 - After)
Estimate for difference:  3.06
95% CI for difference:  (-4.06, 10.17)
T-Test of difference = 0 (vs not =): T-Value = 1.11  P-Value = 0.319  DF = 5 p(0.319) > alpha(0.05)   Unable to Reject the null
```

Figure 28   Data Element Test – Event Utilization Observations
Two Sample T-Test

```
Mann-Whitney Test and CI: IV - Eff G1 and G2 - After, IV - Eff G3 and G4 - Afte N    Median
IV - Eff G1 and G2 - After    6   44.705
IV - Eff G3 and G4 - After    4   40.900

Point estimate for ETA1-ETA2 is 2.050
95.0 Percent CI for ETA1-ETA2 is (-3.233, 9.194)
W = 39.0
Test of ETA1 = ETA2 vs ETA1 not = ETA2 is significant at 0.2410
```

Figure 29   Data Element Test – Event Utilization Observations
Mann-Whitney Test

```
General Linear Model: All Event Utiliz versus Treatment - Patient Files

Factor                    Type   Levels  Values
Treatment - Patient Files fixed       2  A, B Analysis of Variance for All Event Utilization Observati, using Adjusted SS for
    Tests Source                     DF  Seq SS  Adj SS  Adj MS     F      P
Treatment - Patient Files   1   157.4   157.4   157.4  0.48  0.499
Error                      14  4567.7  4567.7   326.3
Total                      15  4725.2

S = 18.0629   R-Sq = 3.33%   R-Sq(adj) = 0.00%

Changes in the treatment (Patient Files) are not associated with changes to the observations (Event Utilization)
```

Figure 30   Statistical Analysis – First Factor (Patient Files)

```
General Linear Model: All Event Utiliz versus Treatment - Group Assignment

Factor                      Type   Levels  Values
Treatment - Group Assignment fixed      4  G1, G2, G3, G4

Analysis of Variance for All Event Utilization Observati, using Adjusted SS for
    Tests Source                         DF  Seq SS  Adj SS  Adj MS     F      P
Treatment - Group Assignment    3   922.0   922.0   307.3  0.97  0.439
Error                          12  3803.1  3803.1   316.9
Total                          15  4725.2

S = 17.8025   R-Sq = 19.51%   R-Sq(adj) = 0.00%

Changes in the treatment (Group Assignments) are not associated with changes to the observations (Event Utilization)
```

Figure 31   Statistical Analysis – First Factor (Group Assignment)

```
Paired T-Test and CI: Time Obs - Befofre, Time Obs - After

Paired T for Time Obs - Befofre - Time Obs - After

N    Mean   StDev  SE Mean
Time Obs - Befofre   6   3.805   0.612   0.250
Time Obs - After     6   1.243   0.648   0.265
Difference           6   2.562   0.917   0.374

95% CI for mean difference: (1.599, 3.524)
T-Test of mean difference = 0 (vs not = 0): T-Value = 6.84   P-Value = 0.001 p(0.001) < alpha(0.05)   Reject the null
```

Figure 32  T-Test Time Parameter

```
Wilcoxon Signed Rank Test: A-B

Test of median = 0.000000 versus median not = 0.000000

N for   Wilcoxon              Estimated
         N    Test    Statistic      P      Median
A-B      6     6         21.0     0.036     2.560
```

Figure 33  Wilcoxon Time Parameter

```
Paired T-Test and CI: Trans Efficiency Obs - B, Trans Efficiency Obs - A

Paired T for Trans Efficiency Obs - Before - Trans Efficiency Obs - After

N    Mean   StDev   SE Mean
Trans Efficiency Obs - B  6    9.24   11.08   4.52
Trans Efficiency Obs - A  6   42.58    4.96   2.02
Difference                6  -33.34   10.30   4.20

95% CI for mean difference: (-44.14, -22.53)
T-Test of mean difference = 0 (vs not = 0): T-Value = -7.93  P-Value = 0.001 p(0.001) < alpha(0.05)   Reject the null
```

Figure 34 T-Test Utilization Parameter (Transportation)

```
Retrieving project from file: 'C:\Users\Gus\Dropbox\Dissertation\PERC
Simulation Results\t Distribution Analysis - Transportation Efficiency.MPJ'

Wilcoxon Signed Rank Test: A-B

Test of median = 0.000000 versus median not = 0.000000

N for  Wilcoxon            Estimated
       N  Test   Statistic    P      Median
A-B    6   6        0.0     0.036    -31.27
```

Figure 35 Wilcoxon Utilization Parameter (Transportation)

```
Session

Wilcoxon Signed Rank Test: A-B

Test of median = 0.000000 versus median not = 0.000000

N for   Wilcoxon              Estimated
      N     Test    Statistic      P      Median
A-B   6     6             0.0    0.036    -36.23 p(0.036) < alpha (0.05)    Reject the null
```

Figure 36  Wilcoxon Signed Rank Test Utilization Parameter (Destination)

```
Session

Wilcoxon Signed Rank Test: A-B

Test of median = 0.000000 versus median not = 0.000000

N for   Wilcoxon              Estimated
      N     Test    Statistic      P      Median
A-B   6     6             0.0    0.036    -7.500 p(0.036) < alpha(0.05)    Reject the Null
```

Figure 37  Wilcoxon Signed Rank Test Patient Safe Evacuations

```
Session

Paired T-Test and CI: Session 1 Utilization, Session 2 Utilization

Paired T for Session 1 Utilization - Session 2 Utilization

N    Mean   StDev  SE Mean
Session 1 Utilization   6    8.05   7.76   3.17
Session 2 Utilization   6    41.91  4.37   1.78
Difference              6   -33.86  8.16   3.33

95% CI for mean difference: (-42.43, -25.29)
T-Test of mean difference = 0 (vs not = 0): T-Value = -10.16  P-Value = 0.000
```

Figure 38  T-Test Event Utilization Parameter

```
Session

Retrieving project from file: 'C:\Users\Gus\Dropbox\Dissertation\PERC
Simulation Results\t Distribution Analysis - Utilization.MPJ'

Wilcoxon Signed Rank Test: A-B

Test of median = 0.000000 versus median not = 0.000000

N for  Wilcoxon         Estimated
       N  Test   Statistic    P   Median
A-B    6    6       0.0    0.036  -33.67
```

Figure 39  Wilcoxon Event Utilization Parameter

AUTOMATED DECISION SUPPORT COMPUTER SYSTEM FOR INFORMATICS CLASSIFICATION AND EVALUATION

CROSS-REFERENCE TO RELATED APPLICATIONS

This application claims priority to U.S. Provisional Application No. 62/550,370, filed Aug. 25, 2017, in which the contents therein is incorporated by references in its entirety.

BACKGROUND

Moore's law predicted that the number of transistors on a computer chip would double every two years while the chip's price would remain constant. "Moore's law" meant consumers could buy the same technology two years later for about the same price. Patrons have come to expect technological products to be faster, cheaper, and more compact over time. This expectation seems to have driven trends of rapid growth in computing power, smaller devices, better battery life, ability to connect to the Internet, and reduction in cost and big data. The age of big data is upon us. There is a need to improve the technological processing of the big data of heath informatics in a new computing era in "connected" healthcare. Cloud computing is becoming increasingly popular. In cloud computing, a cloud may be an aggregation of resources provisioned on demand. Cloud computing may involve cloud resources performing computations instead of, or in addition to, a user's computer. Cloud computing has been compared to a utility, where computing is the service being provided.

The emergency evacuation of a residential healthcare facility is an inherently challenging situation, carrying risk from time-urgency, situation uncertainty, resource constraints, danger to staff, and the need to sustain medical interventions for fragile patients. Multiple disciplines from different professional and corporate cultures attempt to coordinate the evacuation of numerous patients each with unique resource needs while dealing with conflicting terminology, a limited understanding of each other's resource capabilities, fluctuating resource availability, and limited visibility on the needs of the entire patient cohort (Sutcliffe, Lewton, & Rosenthal, 2004; Bovender & Carey, 2006; Taaffe, Johnson, & Steinmann, 2006). Moving a patient even under the best of circumstances is a complex and involved event requiring extensive collaboration between both facilities and the involved EMS. Evacuating an entire patient cohort under duress creates a vast amount of critical patient data that can overwhelm even the best decision-maker (Weiner & Slepski, 2012). There have been a number of prior attempts to address this health informatics problem. Each of these efforts have experienced complications with how to incorporate the patient's medical situation and related resource requirements.

SUMMARY

In light of the foregoing background, the following presents a simplified summary of the present disclosure in order to provide a basic understanding of some aspects of the disclosure. This summary is not an extensive overview of the disclosure. It is not intended to identify key or critical elements of the disclosure or to delineate the scope of the disclosure. The following summary merely presents some concepts of the disclosure in a simplified form as a prelude to the more detailed description provided below.

According to at least one computer hardware and software-based technological embodiment in the disclosure, an automated decision support computer system based on data informatics, includes a first computer readable processing component including a plurality of resource attribute data profiles in which the resource attribute data profiles are generated at least partly from a plurality of electronic computer readable destination records.

A second computer readable processing component includes a plurality of patient classification attribute data profiles in which the patient classification attribute data profiles are generated at least partly from a plurality of computer readable electronic health records. The automated decision support computer system also includes a decision support classification computer engine for scoring and ranking the plurality of resource attribute data profiles with the plurality of patient classification attribute data profiles to generate a computer readable evaluation attribute data profile for display on a computer screen.

In another aspect, the automated decision support computer system includes the decision support classification computer engine having a dichotomous attribute data tables for said scoring and ranking.

In another aspect, the automated decision support computer system includes the plurality of resource attribute data profiles being at least partially generated from a plurality of electronic computer readable transportation resource records.

According to at least one computer hardware and software-based technological embodiment in the disclosure, a Patient Evacuation Resource Classification System (PERCS) is comprised of a computer software-based decision support tool including new classification terms and a series of sub models that identify the most appropriate transportation and destination resources the patient requires for a safe evacuation while minimizing the expenditure of excess resource capabilities applied to each patient movement.

According to at least one computer hardware and software-based technological embodiment in the disclosure, a computer implemented method for a decision support system uses data informatics, the method comprising the steps of: electronically processing a first computer readable database including a plurality of resource attribute data profiles; the resource attribute data profiles being at least partially generated from a plurality of electronic computer readable geo-location destination records; electronically processing a second computer readable database including a plurality of patient classification attribute data profiles; the patient classification attribute data profiles being at least partially generated from scanning a plurality of computer readable electronic health records; processing on, a computer processor, a scoring and ranking engine on the plurality of resource attribute data profiles with the plurality of patient classification attribute data profiles to generate a computer readable evaluation attribute data profile; and displaying on a graphical user interface the computer readable evaluation attribute data profile.

In various aspects of disclosure of a computer technological embodiment, the disclosure includes the concept, original algorithms, original matching protocols, logic paths, data management, original efficiency ranking and recommendation algorithms, reverse-benchmarking algorithms for PERCS. The disclosure introduces an efficiency concept and matching protocols for a software application programming interface (API) with supporting computer algorithms that enables the computer system to expedite the identification of a transportation resource's specific capabilities and of the continued care capacities of predetermined destination facilities. The computer system also provides a unique technological methodology to determine if a specific patient should be accompanied by staff or special equipment/medicines that supplement existing destination and transportation options to achieve a patient safe evacuation.

BRIEF DESCRIPTION OF THE DRAWINGS

Some features are shown by way of example, and not by limitation, in the accompanying drawings. In the drawings, like numerals reference similar elements. The accompanying drawings, which form a part hereof, show examples of the disclosure. It is to be understood that the examples shown in the drawings and/or discussed herein are non-exclusive and that there are other examples of how the disclosure may be practiced.

FIG. 13 is an illustrative block diagram of the processes and functions of certain embodiments of the present disclosure.

FIG. 14 is an illustrative block diagram of a normality test for a prototype implementation of certain embodiments of the present disclosure.

FIG. 15 is an illustrative block diagram of a normality test for a prototype implementation of certain embodiments of the present disclosure.

FIG. 16 is an illustrative block diagram of a normality test for a prototype implementation of certain embodiments of the present disclosure.

FIG. 17 is an illustrative block diagram of a normality test for a prototype implementation of certain embodiments of the present disclosure.

FIG. 18 is an illustrative block diagram of a normality test for a prototype implementation of certain embodiments of the present disclosure.

FIG. 19 is an illustrative block diagram of a normality test for a prototype implementation of certain embodiments of the present disclosure.

FIG. 20 is an illustrative block diagram of a normality test for a prototype implementation of certain embodiments of the present disclosure.

FIG. 21 is an illustrative block diagram of a normality test for a prototype implementation of certain embodiments of the present disclosure.

FIG. 22 is an illustrative block diagram of a normality test for a prototype implementation of the present disclosure.

FIG. 23 is an illustrative block diagram of a normality test for a prototype implementation of certain embodiments of the present disclosure.

FIG. 24 is an illustrative block diagram of a normality test for a prototype implementation of the present disclosure.

FIG. 25 is an illustrative block diagram of a normality test for a prototype implementation of certain embodiments of the present disclosure.

FIG. 26 is an illustrative block diagram of a data element test for a prototype implementation of the present disclosure.

FIG. 27 is an illustrative block diagram of a data element test for a prototype implementation of certain embodiments of the present disclosure.

FIG. 28 is an illustrative block diagram of a data element test for a prototype implementation of certain embodiments of the present disclosure.

FIG. 29 is an illustrative block diagram of a data element test for a prototype implementation of certain embodiments of the present disclosure.

FIG. 30 is an illustrative block diagram of a statistical analysis for a prototype implementation of certain embodiments of the present disclosure.

FIG. 31 is an illustrative block diagram of a statistical analysis for a prototype implementation of certain embodiments of the present disclosure.

FIG. 32 is an illustrative block diagram of a T-Test time parameter for a prototype implementation of certain embodiments of the present disclosure.

FIG. 33 is an illustrative block diagram of a time parameter for a prototype implementation of certain embodiments of the present disclosure.

FIG. 34 is an illustrative block diagram of a utilization parameter for a prototype implementation of certain embodiments of the present disclosure.

FIG. 35 is an illustrative block diagram of a utilization parameter for a prototype implementation of certain embodiments of the present disclosure.

FIG. 36 is an illustrative block diagram of a utilization parameter for a prototype implementation of certain embodiments of the present disclosure.

FIG. 37 is an illustrative block diagram of a rank test for a prototype implementation of certain embodiments of the present disclosure.

FIG. 38 is an illustrative block diagram of a utilization parameter for a prototype implementation of certain embodiments of the present disclosure.

FIG. 39 is an illustrative block diagram of a utilization parameter for a prototype implementation of certain embodiments of the present disclosure.

DETAILED DESCRIPTION

Figure 1:
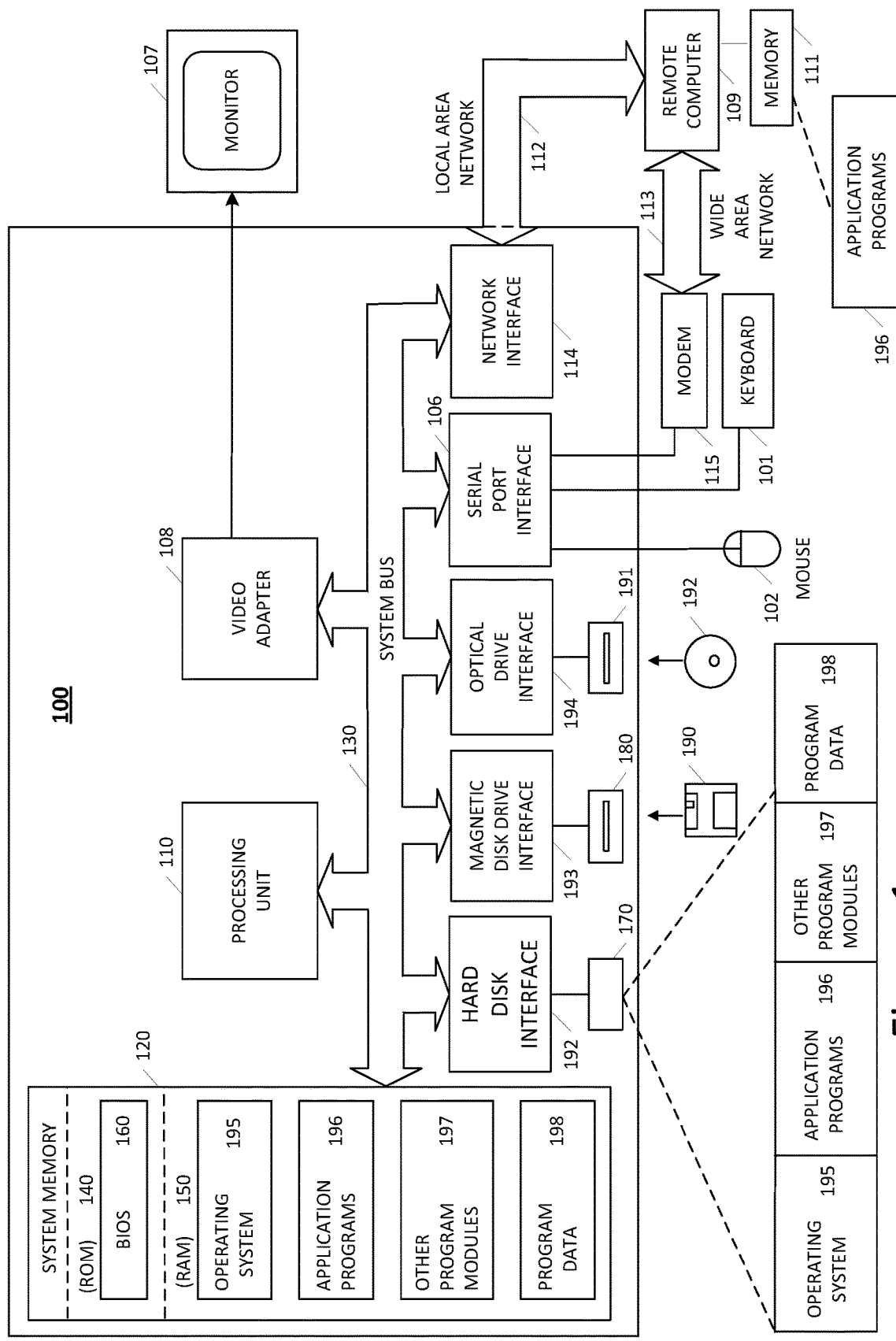
FIG. 1 illustrates a schematic diagram of a digital computing environment for a decision support system in which certain aspects of the present disclosure may be implemented.
Figure 2:
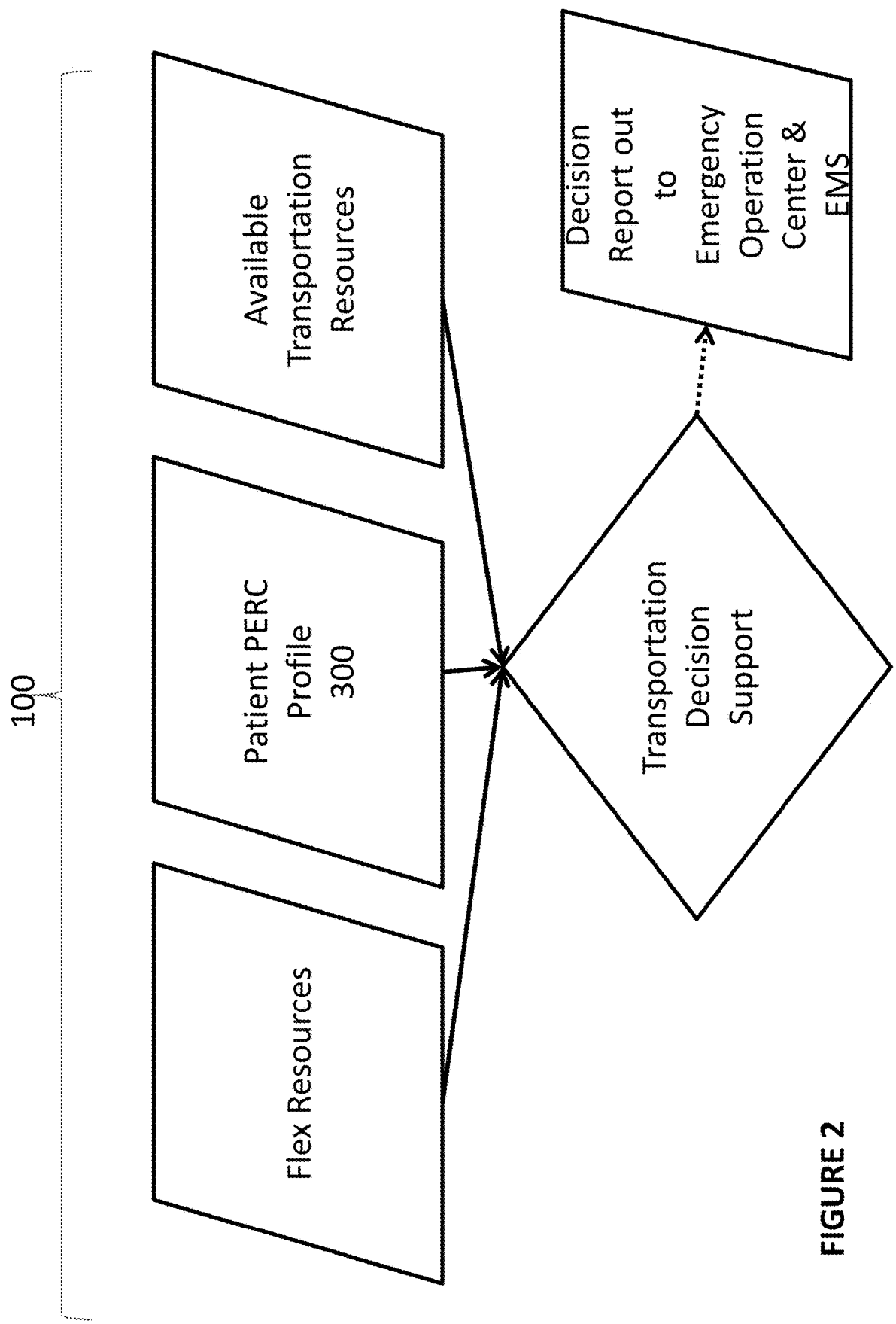
FIG. 2 to FIG. 10 are illustrative block diagrams of workstations, databases, servers and computing devices that may be used to implement the processes and functions of certain embodiments of the present disclosure.
Figure 3:
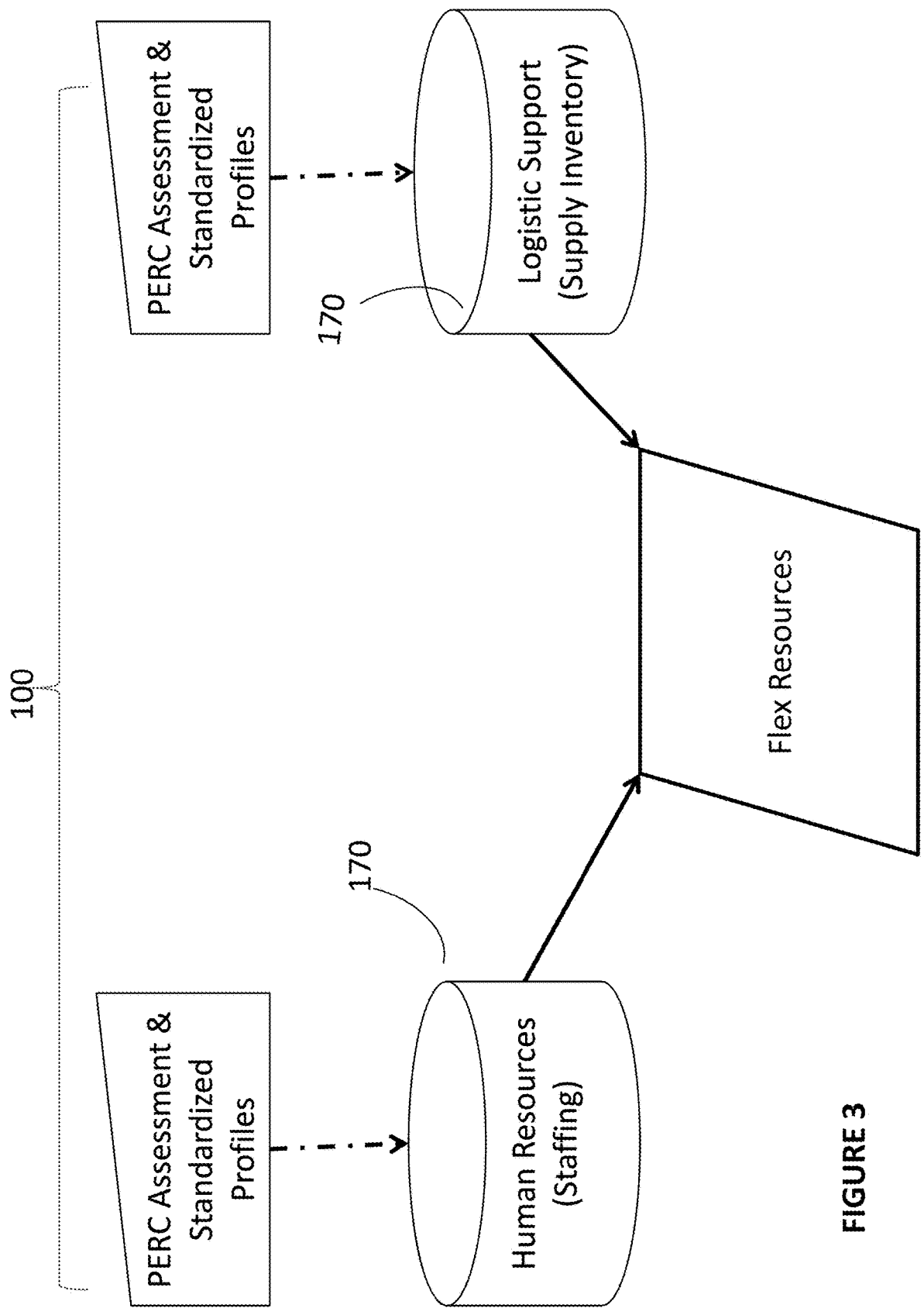
Figure 4:
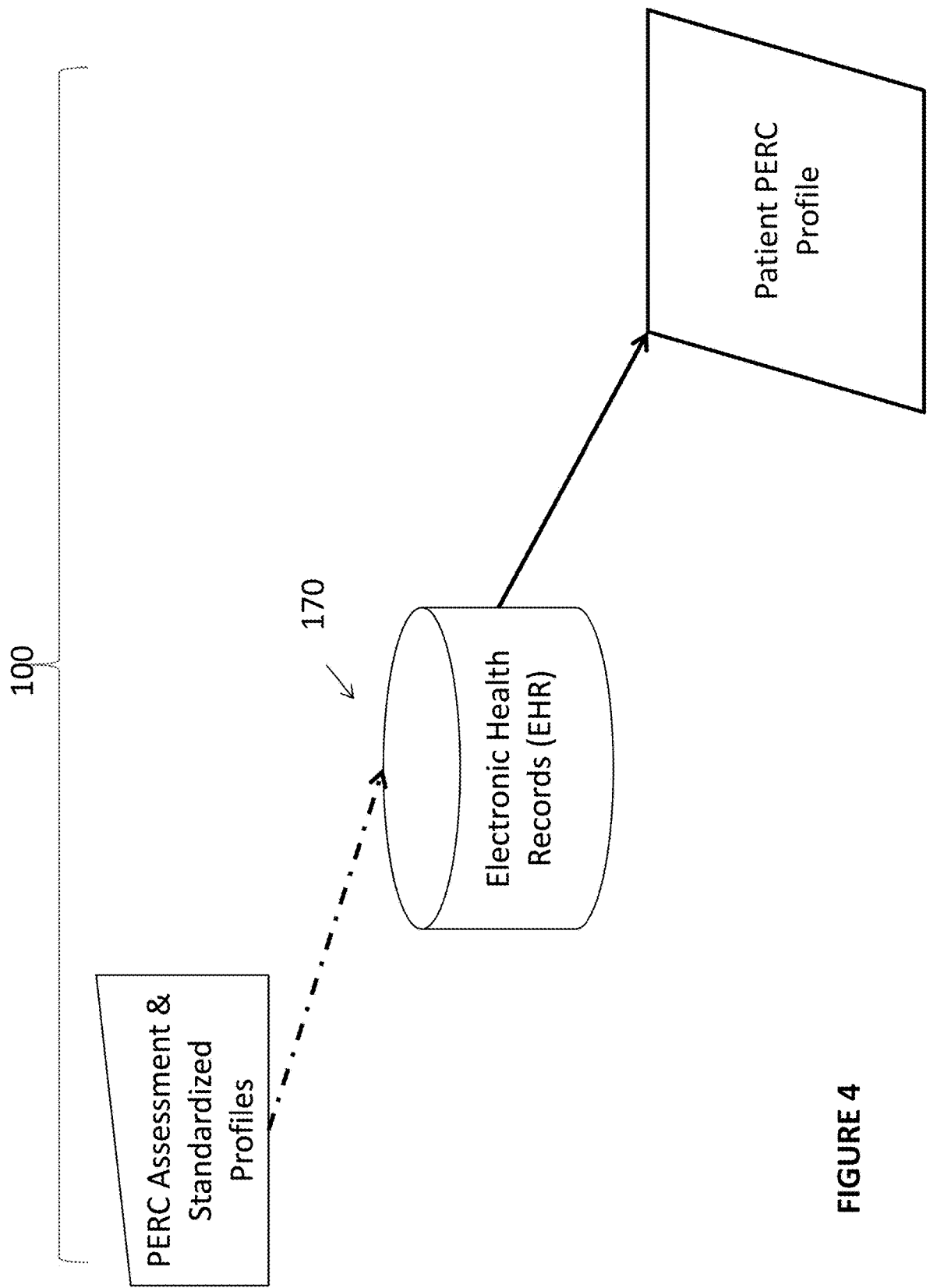
Figure 5:
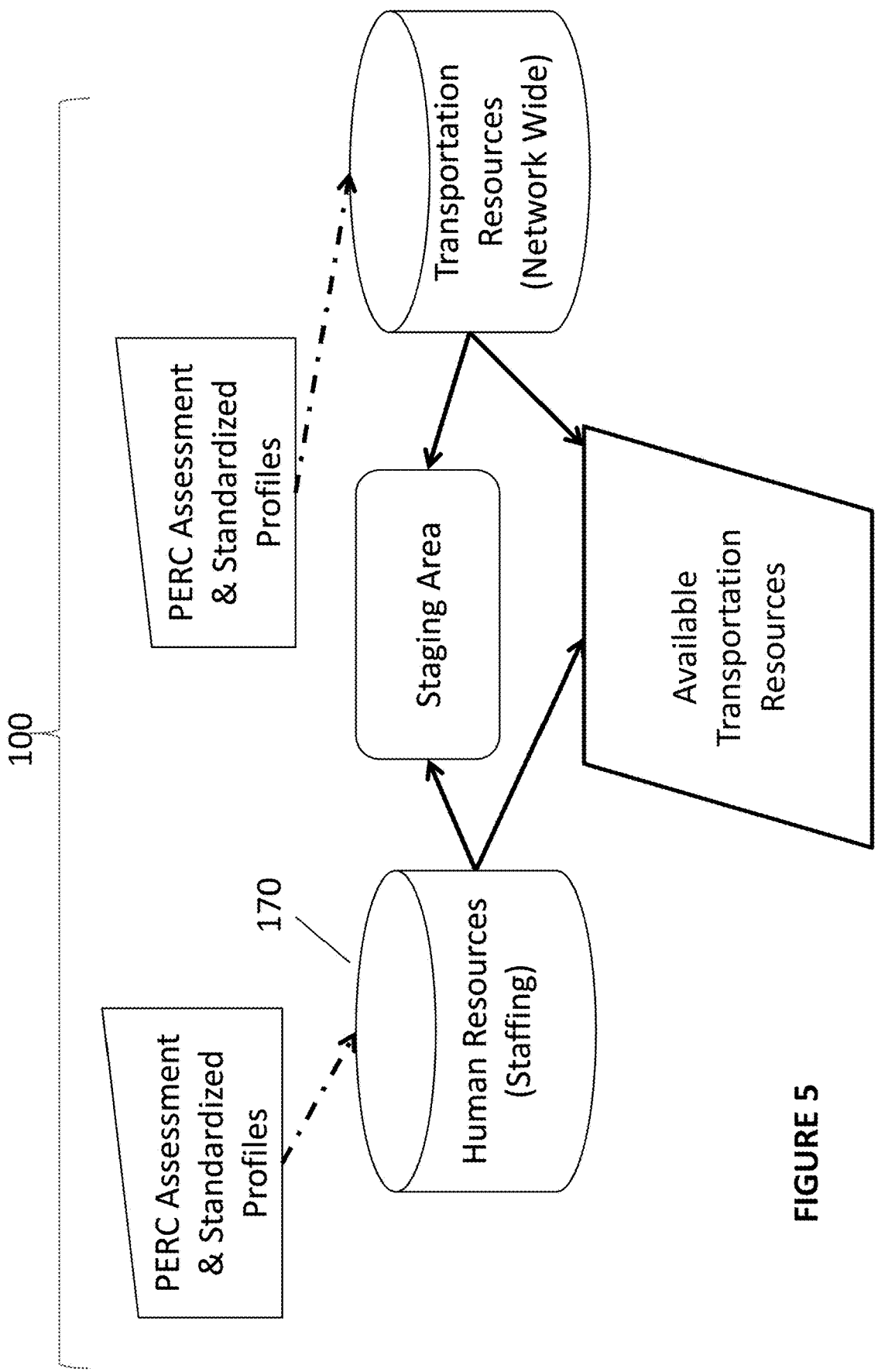
Figure 6:
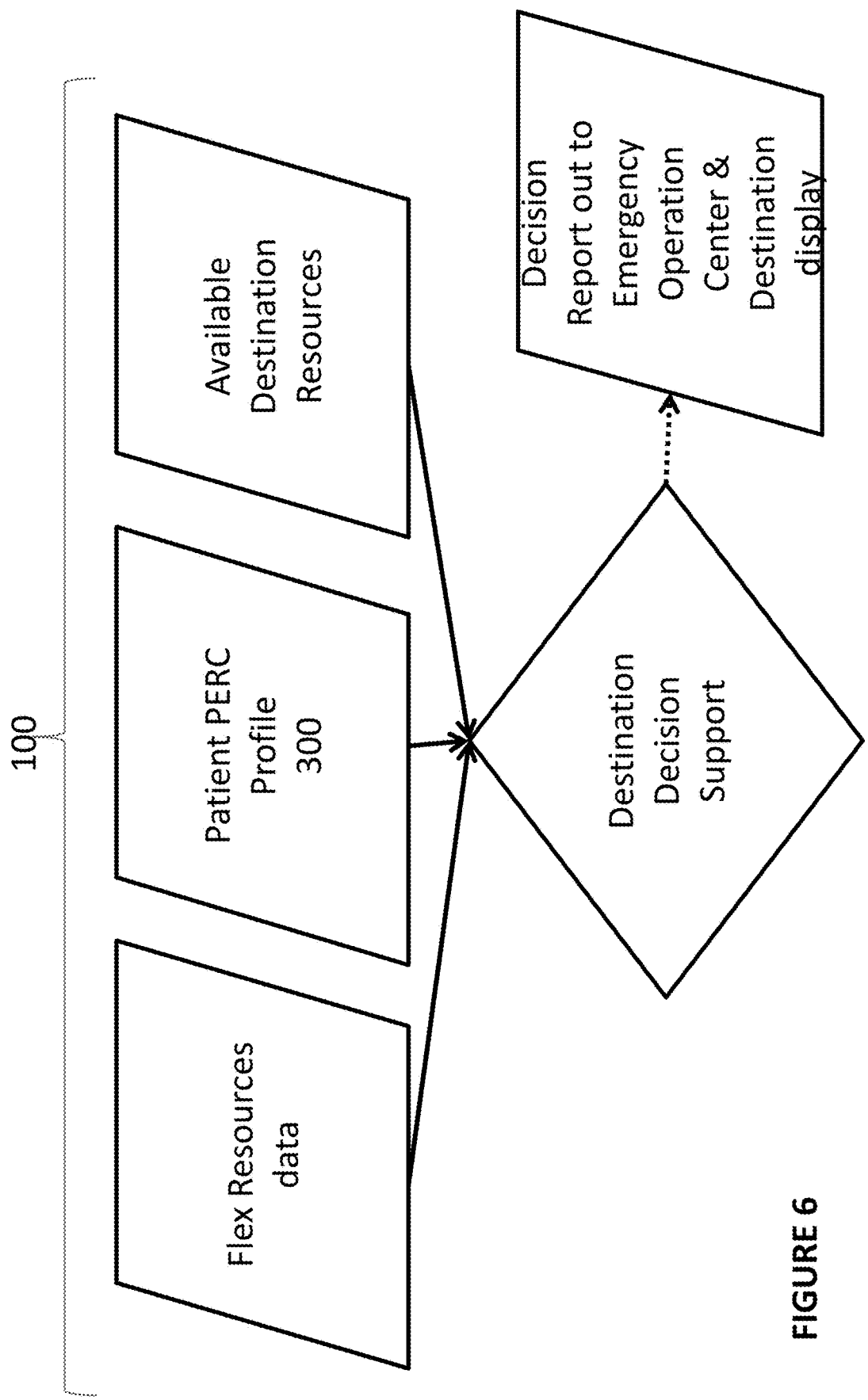
Figure 7:
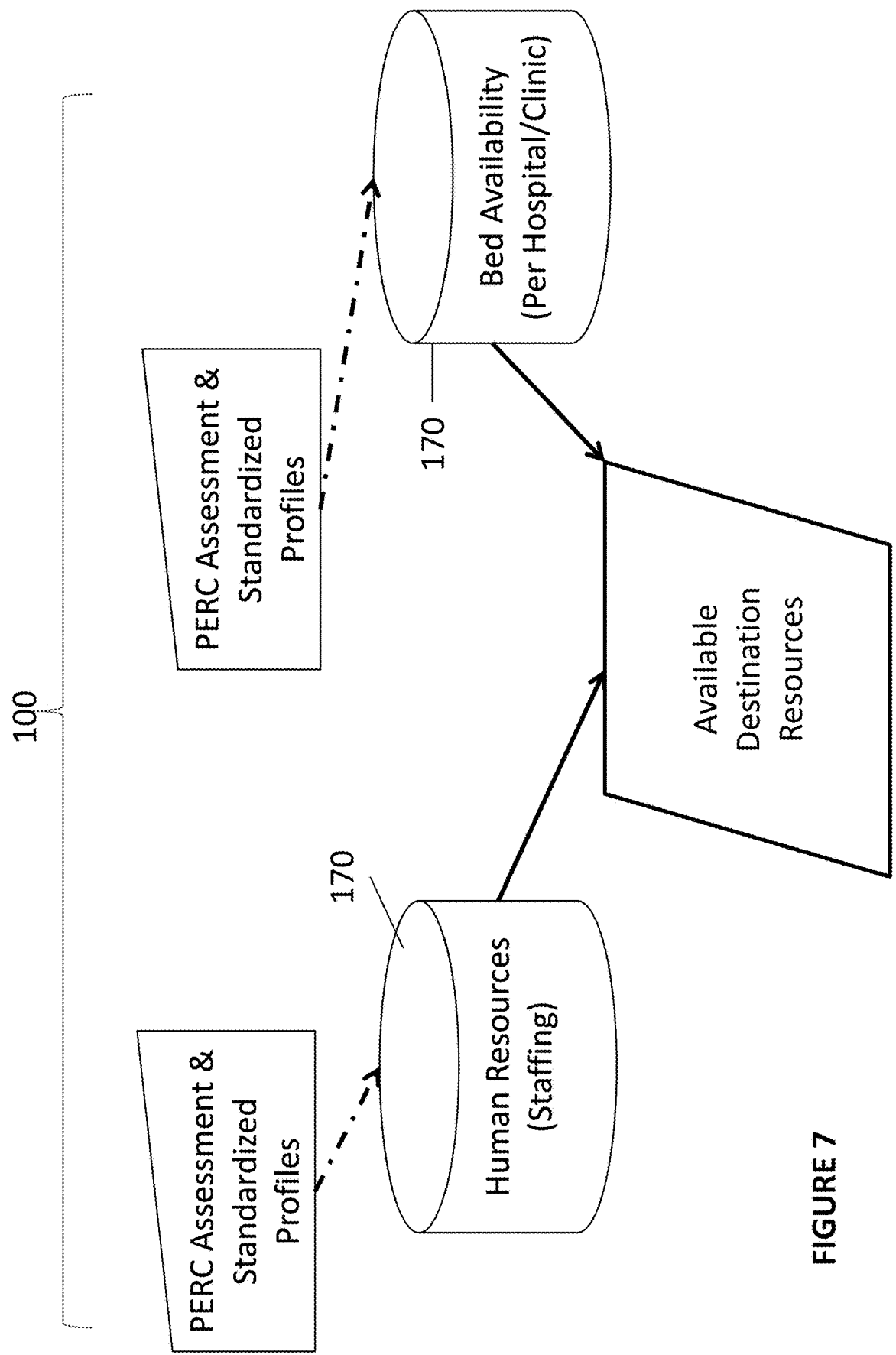
Figure 8:
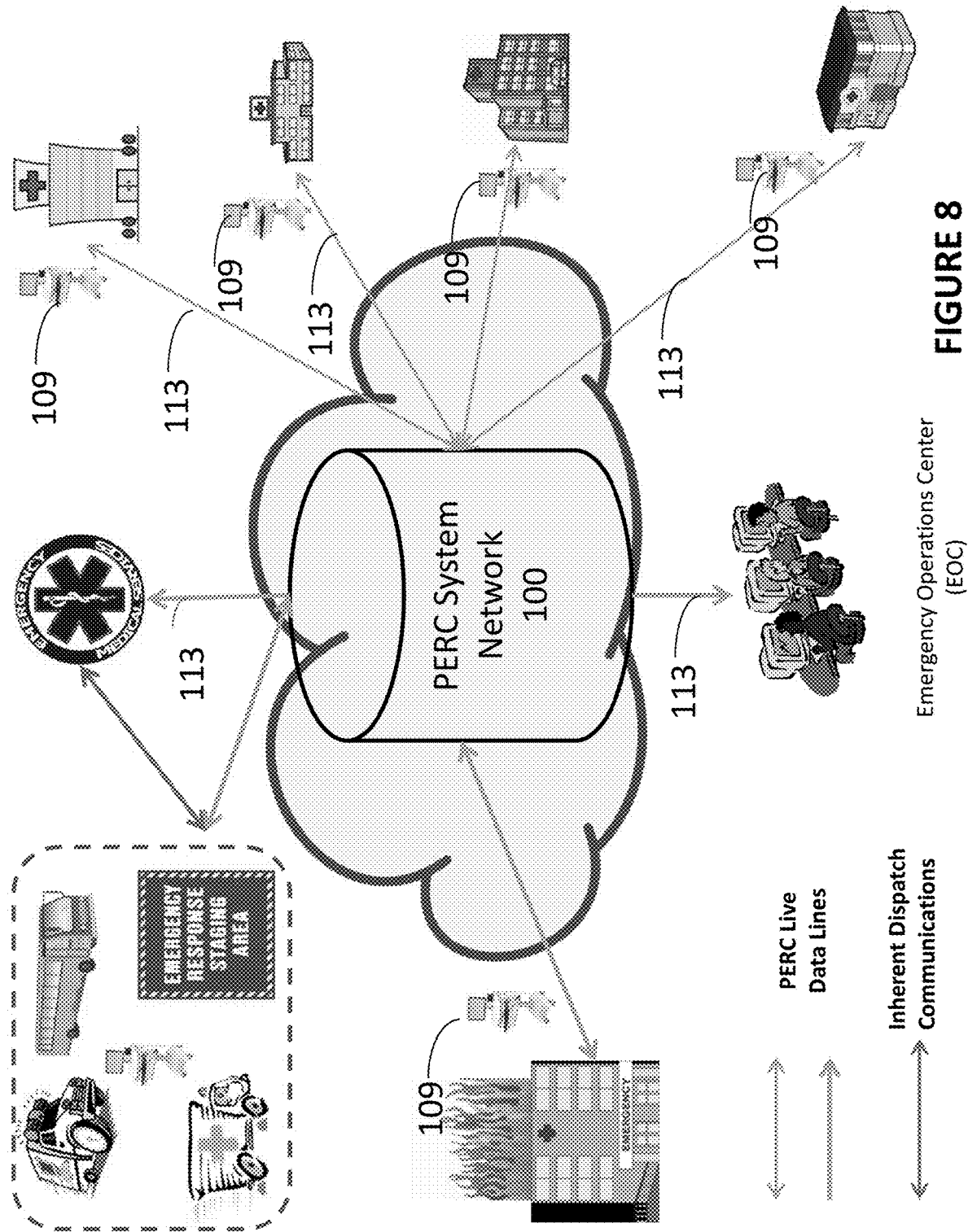
Figure 9:
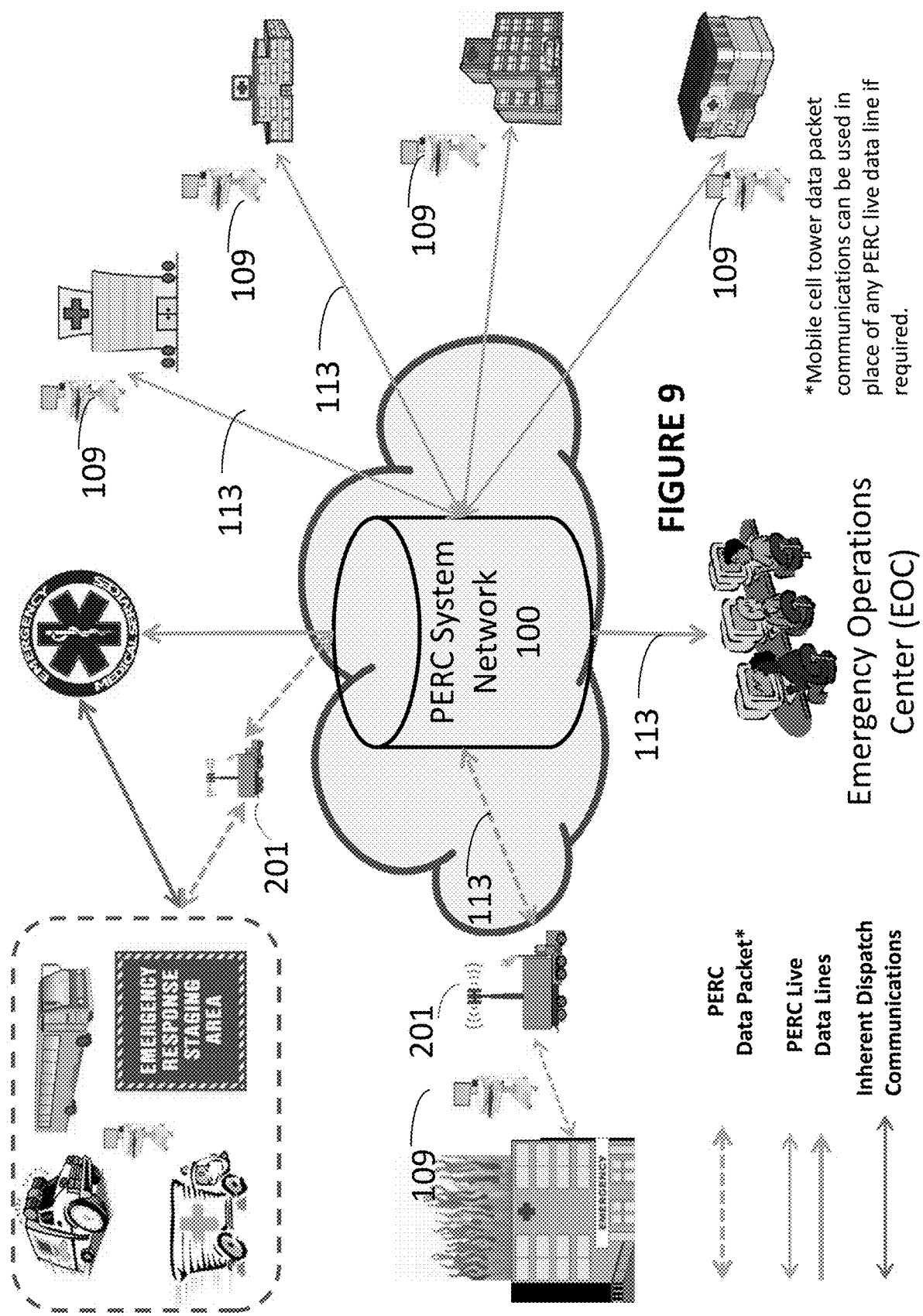
Figure 10:
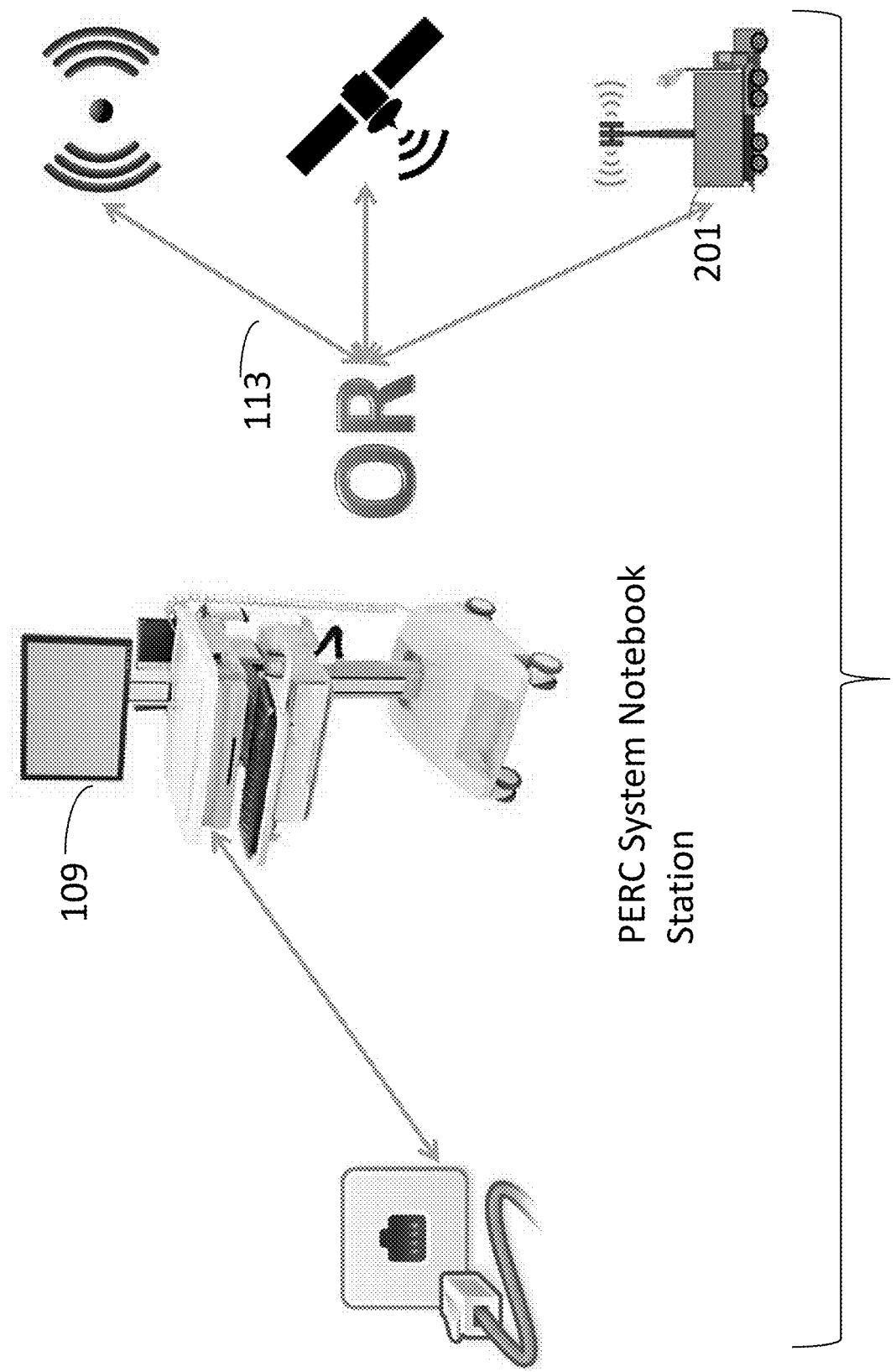

FIG. 1 illustrates a schematic diagram of an exemplary digital computing environment that can be used to implement various aspects of the present invention of the decision support PERCS system. The disclosure is operational with numerous other general purpose or special purpose computing system environments or configurations. Examples of well-known computing systems, environments, and/or configurations that may be suitable for use with the disclosed embodiments include, but are not limited to, personal computers (PCs), server computers, hand-held or laptop devices, smart phones, multiprocessor systems, microprocessor-based systems, set top boxes, programmable consumer electronics, network PCs, minicomputers, mainframe computers, distributed computing environments that include any of the above systems or devices, and the like.

In FIG. 1, a computer 100 includes a processing unit 110, a system memory 120, and a system bus 130 that couples various system components including the system memory to the processing unit 110. The system bus 130 may be any of several types of bus structures including a memory bus or memory controller, a peripheral bus, and a local bus using any of a variety of bus architectures. The system memory 120 includes read only memory (ROM) 140 and random access memory (RAM) 150.

A basic input/output system 160 (BIOS), containing the basic routines that help to transfer information between elements within the computer 100, such as during start-up, is stored in the ROM 140. The computer 100 also includes a hard disk drive 170 for reading from and writing to a hard disk (not shown), a magnetic disk drive 180 for reading from or writing to a removable magnetic disk 190, and an optical disk drive 191 for reading from or writing to a removable optical disk 192 such as a CD ROM or other optical media. The hard disk drive 170, magnetic disk drive 180, and optical disk drive 191 are connected to the system bus 130 by a hard disk drive interface 192, a magnetic disk drive interface 193, and an optical disk drive interface 194, respectively. The drives and their associated computer-readable media provide nonvolatile storage of computer readable instructions, data structures, program modules and other data for the personal computer 100. It will be appreciated by those skilled in the art that other types of computer readable media that can store data that is accessible by a computer, such as magnetic cassettes, flash memory cards, digital video disks, Bernoulli cartridges, random access memories (RAMs), read only memories (ROMs), and the like, may also be used in the example operating environment.

A number of program modules can be stored on the hard disk drive (solid state drive) 170, magnetic disk 190, optical disk 192, ROM 140 or RAM 150, including an operating system 195, one or more application programs 196, other program modules 197, and program data 198. A user can enter commands and information into the computer 100 through input devices such as a keyboard 101 and pointing device 102, such as a mouse or stylus. Other input devices (not shown) may include a microphone, joystick, trackball, game pad, satellite dish, scanner or the like. These and other input devices are often connected to the processing unit 110 through a serial port interface 106 that is coupled to the system bus, but may be connected by other interfaces, such as a parallel port, game port or a universal serial bus (USB), or other serial interface. Further still, these devices may be coupled directly to the system bus 130 via an appropriate interface (not shown). A monitor 107 or other type of display device is also connected to the system bus 130 via an interface, such as a video adapter 108. In addition to the monitor, personal computers typically include other peripheral output devices (not shown), such as speakers and printers.

The computer 100 can operate in a networked environment using logical connections to one or more remote computers, such as a remote computer 109. The remote computer 109 can be a server, a router, a network PC, a peer device or other common network node, and typically includes many or all of the elements described above relative to the computer 100, although only a memory storage device 111 has been illustrated in FIG. 1. Remote computer 109 may be, for example, a desktop computer, a smartphone, a wireless device, a tablet computer, a laptop computer, an IT mobile station and the like, such as a cloud environment. The logical connections depicted in FIG. 1 include a local area network (LAN) 112 and a wide area network (WAN) 113. Such networking environments are commonplace in offices, enterprise-wide computer networks, intranets and the Internet.

When used in a LAN networking environment, the computer 100 is connected to the local network 112 through a network interface or adapter 114. When used in a WAN networking or cloud environment, the personal computer 100 typically includes a modem 115 or other means for establishing a communications over the wide area network 113, such as the Internet. The modem 115, which may be internal or external, is connected to the system bus 130 via the serial port interface 106. In a networked environment, program modules depicted relative to the personal computer 100, or portions thereof, may be stored in the remote memory storage device.

It will be appreciated that the network connections shown are exemplary and other techniques for establishing a communications link between the computers can be used. The existence of any of various well-known protocols such as TCP/IP, Ethernet, FTP, HTTP and the like is presumed, and the system can be operated in a client-server configuration to permit a user to retrieve web pages from a web-based server. Any of various conventional web browsers can be used to display and manipulate data on web pages.

Although the FIG. 1 environment shows an exemplary conventional general-purpose digital environment, it will be understood that other computing environments may also be used. For example, one or more embodiments of the present invention may use an environment having fewer than all of the various aspects shown in FIG. 1 and described above, and these aspects may appear in various combinations and subcombinations that will be apparent to one of ordinary skill.

The disclosure may be described in the context of computer-executable instructions, such as program modules, being executed by a computer. Generally, program modules include routines, programs, objects, components, data structures, etc. that perform particular tasks or implement particular computer data types. The disclosure may also be practiced in distributed computing environments where tasks are performed by remote processing devices that are linked through a communications network. In a distributed computing environment, program modules may be located in both local and remote computer storage media including memory storage devices.

Referring to FIGS. 1 to 10, according to one embodiment, PERCS is designed as a decision support tool system 100 providing visibility on multiple resource choices, displaying their capacity to safely meet the patient's resource needs plus an efficiency score for each to suggest the best match. The system 100 also provides visibility on the patient cohort evacuation process allowing decision-makers to determine how best to use the limited availability of high value resources with robust capabilities such as a scarce Intensive Care Unit (ICU) or a Pediatric Critical Care Truck.

The System 100 is designed to run live as a background process with a dynamic database 170. Each hospital in network would have an IT mobile station where a computer cart is connected to the network and is actively updating. There can be multiple iPads, table computers, laptops, or notebooks on the cart that would be synched with the hard drive 170 through docking stations. Once deployed, the iPads, table computers, laptops, or notebooks interact with the system via WiFi or Bluetooth connection or other wireless network connections to provide each user with access to the current patient census, ambulance availability at the staging area, and updating bed space availability with supporting network cloud of hospitals.

As the crisis unfolded and the evacuation progressed, the System 100 would provide live or real-time updates on the status of the patient census from the evacuating hospital allowing external support cells to monitor the pace of the evacuation. This could include the Emergency Operating Center allowing these centralized personnel to monitor the evacuation and potentially identify any impending bottlenecks (logistical, staffing, transportation, etc.). In the event of a network failure, the hard drive on the IT cart 109 would have the most current hospital census. Database 107 updates would have to shift to data packet uploads and downloads using improvised cell tower transmissions or improvised COWs (Cell on Wheels) 201.

Referring to FIGS. 1 to 10, datamining protocols can be provided as an application programming interface (API) customized for each healthcare coalition, as each participating facility may have different electronic healthcare records systems, unique terminology, contrasting cultures, and/or multiple languages.

This technical disclosure contributes to knowledge of how the most vulnerable in our community, individuals in the care of a residential healthcare facility, can be safely evacuated from a pending crisis or disaster affected area. It is motivated by a personal core belief that a society can be measured by how it treats the most vulnerable of its people. Governments and organizations come to the aid of their people at times of crisis and implement plans to move them from harm's way, but too often the response and the plans for evacuation focus solely on the general population, seldom providing the additional resources necessary to help the vulnerable. Researchers focused on the evacuation of special needs groups have advocated that any plan that enables the safe evacuation of this most vulnerable part of our population will have mustered more than sufficient resources and mastered event timelines to then evacuate the general public in good order. In much the same way, providing a solution to overcome the complications associated with evacuating a residential healthcare facility could enable a method for matching resource needs to resource capabilities that could help make the most of limited equipment and resources, improving the community's overall resilience.

This disclosure provides for emergency evacuations of hospitals and residential healthcare facilities with a Patient Evacuation Resource Classification System (PERCS) as an automated decisions support tool of new classification terms and a series of sub models that identify the most appropriate transportation and destination resources the patient requires for a safe evacuation while minimizing the expenditure of excess resource capabilities applied to each patient movement. According to one technological aspect of the disclosure, the PERCS enables a requirements analysis of the process and enables an evidence-based computer model that accurately identifies patient resource requirements translatable to resource capabilities.

This disclosure provides a significant contribution to the technical of knowledge with the presentation of the new computer hardware and software-based Patient Evacuation Resource Classification System (PERCS) for emergency evacuation of a residential healthcare facility and the method for development of patient classification terminology. This effort is significant because no previous effort to capture this level of granularity has been published. Even the most recent efforts with Hospital Availability Beds (HAvBED) categories has noted lapses that omit patient criteria and is considered too broad to effectively manage patient evacuations. PERCS significantly improves efforts to predict hospital costs associated with emergency evacuation, more specifics on how staffing will be impacted by the evacuation process, and even enhance the determination of risks incurred by evacuating individual patients. PERCS also provides greater transparency with surge bed availability at destination facilities and identify possible supplemental staffing requirements. Finally, PERCS identify potential shortfalls in emergency medical service (EMS) equipment and personnel that could hamper an evacuation. Given the scope of information provided, PERCS could support certificate of need application evaluations.

This disclosure is also significant for its use of Systems Engineering and Engineering Management (SEEM) tools in innovative ways to develop objective, context-specific descriptions and a relational framework that provides real-time decision support. This unique application of SEEM fundamentals enabled the research to conduct an in-depth analysis of a very complex event identifying system functions and relationships, which supported the creation of a new comprehensive construct and system architecture.

In this disclosure, a computer-based decision support tool increases the efficiency in matching complex patients with safe transportation and appropriate destination resources during an emergency hospital evacuation, while maintaining patient safety and evacuation efficiency for both the individual patient and the aggregate patient population.

In this disclosure, a computer-based decision support tool uses a dynamic database 170, identifies and incorporates individual patient-care needs and presents appropriate matching of individual patients, based upon their medical needs, with available transportation resources and their capabilities to safely evacuate the patient and transfer him/her to a destination with adequate healthcare resources providing the necessary continued care. The system is intended to increase efficiency for the individual patient matching decision, the aggregate matching decisions, and the evacuation effort for the entire patient cohort by also increasing transportation fleet and destination facility utilization rates during the emergency evacuation.

The PERC System is at least one implementation can be generally broken down into various parts, including the scoring algorithms that, in one construction, may be based on Gower's General Coefficient of Similarity and the attribute tables originated from this disclosure in the foregoing. When combined, according on the disclosure, a new mathematical concept of/for dichotomous tables that can translate between requirements and capabilities. This new concept can be applied in the healthcare industry for programs other than patient movement and can be applied to other industries as well to address transportation, inventory management, parts assembly, facility capabilities, and to test proposed efficiency recommendations.

This new mathematical tool can be adapted to use with a variety of systems where the requirements for any given item or person must be paired or matched with another item or person (resource) that possess the necessary capabilities. The tool also provides visibility on the range of options to consider among available resources and the efficiency for each option under consideration, the situational awareness feature to understand the consequences of that pairing, and the flex resource feature that provides supplemental options to make the most of all inherent systems and assets.

This new mathematical tool will be referred to as Ventura's Principles for Dichotomous Tables (VPDT). Before applying VPDT, if desired, each industry application may have a functional analysis and allocation using a requirements analysis, which would provide the engineered functional decomposition results. These results would identify the attributes that could be considered for the development of the dichotomous tables. Unlike the Coefficient of Similarity where the characters defined are fixed as with taxonomic classifications, this instant disclosure's dichotomous tables contain characters that are transitional or "dual-phase" where the same attribute can represent a requirement or a capability. The dual-phase nature captured by this disclosure includes attributes that are also scalable and offer multiple group and sub group options to address specific details or qualifiers, such as a specific medication within a formulary or a specific gas under medical gases (i.e. oxygen, etc.). In other industries, the dual-phase characters could be represented as unique handling requirements such as refrigeration for perishable foods or delicate electronics, as well as, representing the inherent capability of either climate controlled or refrigerated transportation and/or storage (this would also include the potential flex resource that could be added to those resources to allow them to qualify as acceptable storage or transportation, i.e. portable A/C unit, fan cooling systems, etc.). Another example would be a requirement for security escort or a package requiring waterproofing that would also represent the appropriate security capabilities for a given facility or the identification of a shrink-wrap requirement for package delivery. VPDT can be applied to each critical stage of any complex program or system as defined by a current or proposed construct and directly testable through prototype.

The new dichotomous attribute tables would be developed in a similar manner as described in this disclosure where one table would display the requirements represented by the item or individual in need (i.e. patient, special delivery package, raw materials, military personnel, hospital staff, etc.) and the other tables would represent the different kinds of capabilities available to meet those needs. Each capability table could represent multiple variants of that unique capability (i.e. in addition to ambulances within ground transportation or heart transplant patients among organ transplant patients, this can also represent climate-controlled spaces within warehouses, bulk transport within maritime transportation, specialized units within military facilities, clinics within treatment facilities, engine repair workshop within repair facilities, IT skill sets among vendors, etc.).

VPDT can serve as a powerful tool for those engineering proficiencies tasked with reviewing, auditing, and improving existing systems, modes of operations, and/or business practices. Once the initial functional analysis is completed, each engineering proficiency is traditionally tasked to determine where inefficiencies exist and/or how to improve critical decision-making. In many cases (as with patient movement), decision-makers are presented with a multitude of variables that would influence their choices. As noted previously in this disclosure, processing overwhelming data can be as big a challenge for decision-makers as working with too little or no data. VPDT would assist in identifying the attributes or decision impacting data and organize the results to maximize the decision-makers chances for making the best possible choice.

By applying VPDT, the various engineering proficiencies can also develop prototypes and/or functional models of proposed changes that would test and even quantify the impact of recommendations proposed. These simulations could opt to provide a limited number of options to the decision-maker or choose to display all options and their respective efficiencies and/or strengths as related to the requirement or need. In many cases as with Certificates of Need, VPDT would provide the first and only quantifiable justification for procurement, expansion, or new development of capabilities Effectiveness can be defined in one instance as maintaining patient safety by meeting their medical requirements while improving the efficiency of the evacuation effort at the individual patient level and for the patient cohort and/or improving utilization of high value/low availability resources. Effectiveness can also be defined by an industry standard for the given requirements analysis and engineered decomposition.

For the purposes of this disclosure, patient safe means that at a minimum all of the patient's medical needs represented in their PERC attribute profile data are met by the transportation resource and the appropriate destination facility capable of providing continued care.

A patient safe resource is defined as a resource that maintains patient safety and at a minimum meets all of the patient's medical needs represented in their PERC attribute profile data.

A patient's PERC attribute profile is the quantitative representation of a given patient's medical needs using the computer readable data attributes developed for the PERC system.

A transportation, destination or flex PERC attribute profile is the quantitative representation of that resource's capabilities using attributes developed for the PERC system. It should be noted that the destination resource may have a computer readable geo-location attribute data, such as a global positioning system (GPS) data for temporary locations as well as building structures.

The sample data elements are outlined in Table 3-1. In the "attribute data" for the various PERCS profiles includes ASCII characters in computer readable form or complied data. The ASCII characters can be manipulated in the software for the decision support system.

TABLE 3-1

Sample Data Elements
Data Element $t_{k_1}$-Time parameter transportation
$t_{k_2}$-Time parameter transportation
$t_{d_1}$-Time parameter destination
$t_{d_2}$-Time parameter destination
$t_{\alpha_1}$-Time parameter patient allocation
$t_{\alpha_2}$-Time parameter patient allocation
$e_{k_1}$-Efficiency parameter transportation
$e_{k_2}$-Efficiency parameter transportation
$e_{d_1}$-Efficiency parameter destination
$e_{d_2}$-Efficiency parameter destination
$f_{k_1}$-Flex parameter transportation
$f_{k_2}$-Flex parameter transportation
$f_{d_1}$-Flex parameter destination
$f_{d_2}$-Flex parameter destination
$PS_1$-Patient Safe Evacuation
$PS_2$-Patient Safe Evacuation
$U_{k_1}$-Utilization parameter transportation
$U_{k_2}$-Utilization parameter transportation
$U_{d_1}$-Utilization parameter destination
$U_{d_2}$-Utilization parameter destination
$U_{v_1}$-Event utilization parameter
$U_{v_2}$-Event utilization parameter In at least one construction, the Patient Evacuation Resource Classification (PERC) System can be produced in five phases: 1) functional analysis and allocation for identification of patient medical conditions of relevant concern for an emergency facility evacuation, 2) the use of the functional architecture for the development of the PERC Construct, 3) Use of Design Synthesis for the creation of a PERC Model and Prototype, 4) expert elicitation for the model evaluation and assessment, and 5) expert judgment through simulation for the proof of concept PERC Construct and Functional Architecture The PERCS tool 100 facilitates rapid but appropriate matching of individual patients, based on their medical need categories, with available transportation resources and available healthcare destinations to safely evacuate and transfer the patient to an adequate healthcare facility for continued care. The system is intended to increase efficiency for the individual patient matching decision, the aggregate matching decisions for the evacuating cohort, and the overall evacuation effort by increasing utilization rates for available and safe transport and destination resources during the emergency evacuation.

Referring to FIG. 1-10, the PERC Construct principles specifically developed are:

Identify Patient Medical Conditions using an Electronic Healthcare Record (EHR) scan.

Create a PERC Patient Profile translatable to safe transportation resource and destination resource capabilities Categorize/standardize transport and destination resources so they can be assessed against patient needs.

Identify the role of staff skills (Paramedic, ICU Nurse, etc.) and their relationship to equipment availability, as well as, how they influence resource capability reporting.

Categorize/standardize event available flex resources (staff, equipment, medications, supplies, etc.) so they can be assessed against shortfalls with meeting patient needs by either transport or destination resources.

Identify "Patient Safe" resources and resources that can be augmented to become "Patient Safe".

Provide situational awareness when considering utilization of a scarce resource by presenting the potential need for that resource by the remaining patient cohort.

Provide an efficiency rating for a resource assignment by comparing the patient profile against each available "Patient Safe" resource.

Maintain a record of resource allocations and adjust the remaining resource availability for each successive patient.

Characterization of Patient Healthcare Needs

Figure 11:
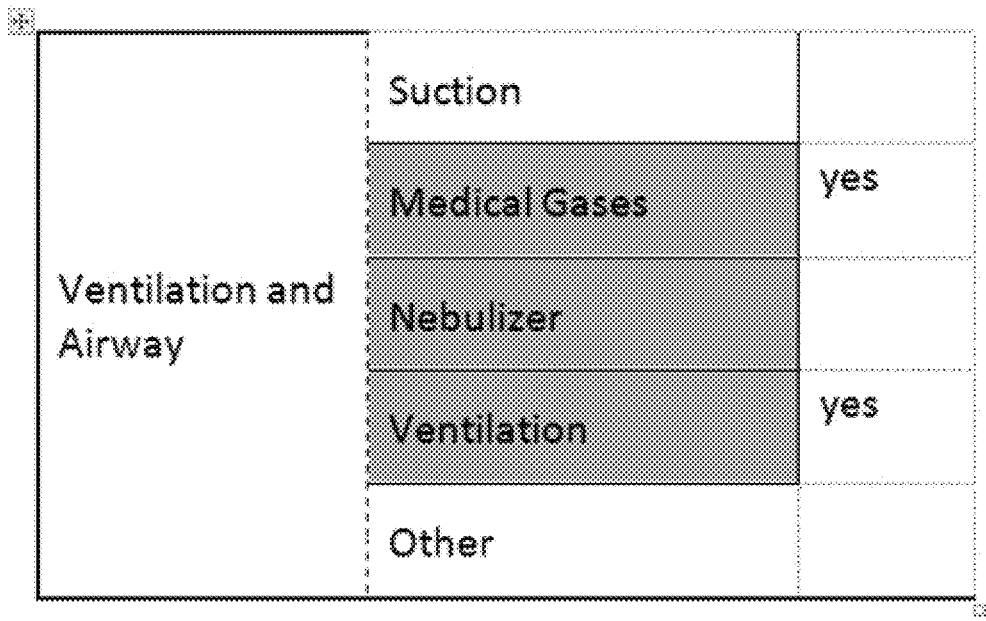
FIG. 11 is an illustrative block diagram of the processes and functions of certain embodiments of the present disclosure.

For the purposes of this disclosure, patient healthcare needs were defined by designated resources required to maintain the patient safe during transit and upon relocation to a new destination for continued care. These needs were not defined by a patient's medical diagnosis, but by the identified resources and protocols that were successfully keeping the patient medically safe and stable at their current facility. For example, the fact that a patient has asthma is not sufficient information to define the patient PERC profile unless details of the patients □ condition indicated whether he/she required a ventilator, medical gases, and/or aspiration prevention. These resource requirements were identified in the Ventilation and Airway category of the patient PERC profile (as shown in FIG. 11) and were reflected by a positive response (yes) or a check (√) next to the specific patient resource need.

The transportation and/or destination resource tables considered safe for meeting this patient medical resource need had either one, several, or all of those boxes checked as well to indicate that they could support these medical resource needs with their specified resource capabilities reflected as onboard or inherent ventilators, medical gases and/or a qualified medical professional with access to suction. This disclosure also considers supplemental equipment and staffing to add to the resource capabilities of an existing transportation resource, which is discussed later in this under Flex resources.

Characterization of EMS Transportation Resource Capabilities

An audit and assessment of these transportation resources (during preparedness) generated a transportation resource PERC profile for each transport vehicle in a fleet, based upon the capabilities of the resource including the inventory of equipment required onboard for a given certification (BLS, ALS, CCT, etc.), the medications each is required to carry, and the skill sets of the EMS personnel assigned (Paramedic, Basic, Enhanced, etc.). Combined, these resource capability responses created a transportation resource PERC profile that was matched against a patient's PERC profile. For example, the transportation resource PERC profile for a Pediatric Critical Care Truck (PCCT) reflected this resource's capabilities and had positive responses (Yes) or a check (√) next to most of the pediatric related attribute types and to most of the intensive care related attribute types, thus it was a top contender for a pediatric intensive care patient who would present those patient resource needs. Similarly, a Bariatric capable ALS ambulance had a positive check (Yes) or a check (√) next to the bariatric weight and for all other medical attributes related to emergency intervention, and was a likely contender for a bariatric intensive care patient or a post-op bariatric patient who presented those patient resource needs.

Characterization of Destination Resources Capabilities

The destination resources were defined by their in-hospital locations (ward/specialty care), their specific capabilities (bariatric capable beds, restraints, etc.), the equipment and logistics available to that location (ventilators, medical gases, bariatric winch, etc.), and the medical professionals available to that ward (ICU, Cardiac, Oncology, etc.). Each destination resource had a unique PERC profile that is used to match against the patient PERC profiles of evacuating patients. For example, a Neonatal Intensive Care Unit space at a coalition hospital had a destination resource PERC profile reflecting positive responses (Yes) or a check (√) next to most of the pediatric attribute types and most intensive care unit attribute types, thus a Neonatal ICU patient from the evacuating hospital was considered for this space since they presented those patient resource needs. Since patient transfers placed each individual at greater risk of injury and medical complications, the logic for building a destination resource table was to help decision-makers find the right place capable of continuing patient safe care and minimize the need for a second transfer to another facility. Combining this decision process with the transportation resource allocation also promoted improved utilization of all available resources (i.e., those staged and ready for use).

Figure 12:
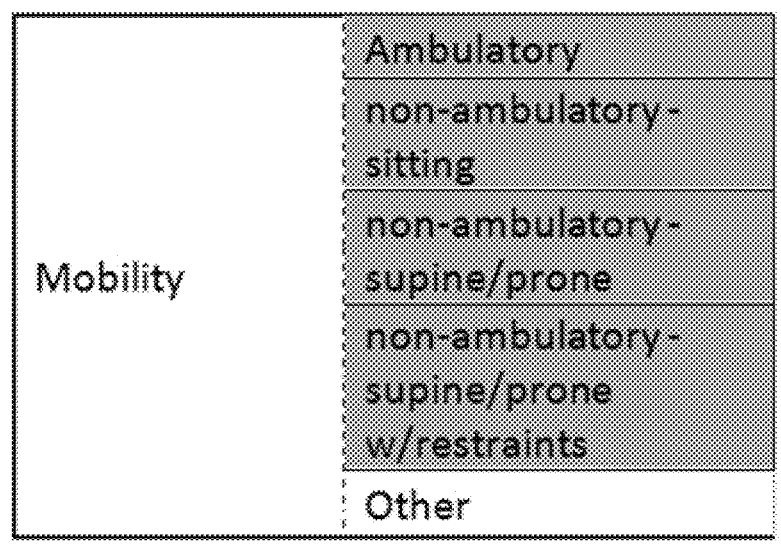
FIG. 12 is an illustrative block diagram of the processes and functions of certain embodiments of the present disclosure.

A list of data attributes was organized so that a general attribute category contained the relevant attribute types. An example of this organization can be seen in FIG. 12 which is an excerpt of the full attribute table. As shown, the general category identifies those patient issues related to mobility. The associated attribute types indicate the specific patient resource needs, based on the patients medical condition that will affect the evacuation process and the allocation of the appropriate resources. It is noted that the attribute type concept is that each is translatable between patient condition/medical need (resource needs) and resource capabilities defined by each resource's associated supplies, equipment and personnel.

PERC Model and Prototype

This prototype contains four attribute tables (Patient, Transportation, Destination, and Flex Resources) along with originally designed algorithms that accurately match a set of patient attributes to available patient safe transportation and patient safe destination resources. The patient-attribute table categorizes the criteria necessary to represent each patients medical information, now translated to a form where it can be matched to available patient-safe transportation resources and patient safe destinations, including flex resources adapted to provide patient safe situations.

The disclosure also includes the protocols, terminology, logic paths, and user guidelines for creating a testable PERC system. The testable system or PERC Prototype provided an opportunity for user interface that allowed for a more comprehensive understanding of the PERC System capabilities and proposed applications.

The attribute tables are one of two components of the PERC Model and Prototype. The specific attribute types used to build the tables and the way each were organized were pivotal in developing four distinct computer readable data tables representing two distinct concepts (needs versus capabilities) that employed a common framework. This common framework allowed direct comparisons between a patient's medical resource needs and the resource capabilities of any given transportation, destination, or flex resource. To achieve this, the first attribute table was constructed to represent the patient cohort being evacuated. Each column of the table represents the individual patient resource needs within a patient PERC profile (j=1, 2, 3, 4, . . . etc). Using datamining protocols identified for each Electronic Health Record (EHR) system, an automated PERC system fills in each patient's profile in accordance with the PERC attribute types. Each patient PERC profile x is defined as $x = \{x_{(i=1,j)}, x_{(i=2,j)}, \ldots x_{(i=1,j)}\}$, where the symbol $x_{(i,j)}$ represents a patient profile relative to the PERC attribute types listed, with i representing the specific index numbered PERC attribute type and j the value (or condition) of the patient when compared against i. The list of patient resource needs required by their indicated conditions for each of the attribute types for one patient becomes that patients PERC profile.

A second attribute table was constructed to represent transportation resources available $T_{(i,t)}{}^n$ allowing for ground transportation resource PERC profiles, where (t) represents the value or capabilities of the specific transportation resource when compared against the PERC attribute type (i), and (n) represents the total number of transportation resources available. The list of indicated capabilities for each of the attribute types for one transportation resource becomes that transportation resources PERC profile.

A third attribute table was constructed to represent destination resources available $D_{(i,d)}{}^n$ allowing for destination resource PERC profiles, where (d) represents the value or available healthcare capability of the specific destination resource when compared against the PERC attribute type (i), and (n) represents the total number of destination spaces in network. The list of indicated capabilities for each of the attribute types for one destination resource becomes that destination resources PERC profile.

A fourth attribute table was constructed to represent available $R_{(i,r)}{}^n$ allowing for flex resource PERC profiles, where (r) represents the value or capability of the specific flex resource against the PERC attribute type (i); (n) represents the number of flex resource options available for the evacuating hospital. In one example, the flex resources are those made available by the evacuating hospital. Network or coalition emergency supplies or resources will can be includes in other implementations. For example, sending qualified healthcare personnel and equipment to a receiving destination will supplement the destination PERC profile and thus allow a "match" with the patient PERC profile. The list of indicated capabilities for each of the attribute types for one flex resource becomes that flex resources PERC profile.

Observations are typically broken down by scale (interval, ordinal and nominal) and also by range set (continuous and discrete). Given that the PERC values for j, t, d, and r (unique attribute type observations for each table) are limited to either YES or NO answers. All PERC Attribute types are defined as Nominal and Discrete. For example, a patients weight is on a continuous scale, but is converted to the relevant nominal category to create a nominal attribute value. The same is done for a patient's age. This approach better reflects the medical professional categories for specialized care; for example the category "Neonatal Care" becomes 0-28 days old, or Bariatric Care is a category of patients weighing more than 450 lbs.

Mathematical Expressions for Nominal—Discrete Attributes

As Nominal and Discrete attributes, the following expressions can be used to calculate the similarity between two—profiles:

when comparing a patient profile record to a transportation resource:

$$f_{nom}(x, t) = \begin{cases} 1 & \text{if } x_{(i,j)} = t_{(i,j)} \\ 0 & \text{otherwise} \end{cases}$$

when comparing a patient profile to a destination resource:

$$f_{nom}(x, d) = \begin{cases} 1 & \text{if } x_{(i,j)} = d_{(i,j)} \\ 0 & \text{otherwise} \end{cases}$$

when comparing a patient profile to a flex resource:

$$f_{nom}(x, r) = \begin{cases} 1 & \text{if } x_{(i,j)} = r_{(i,j)} \\ 0 & \text{otherwise} \end{cases}$$

Development of Scoring Algorithms for PERC Profile Comparison

The PERC System values and expressions created for each scoring algorithm are based on Gower's principles to calculate scores and validity of dichotomous characters as shown in Table 2 below (Gower, 1971). This Figure presents three values to be considered, 1) Benchmark Record value, 2) Match value, and 2) Response value.

A benchmark PERC profile is the primary profile compared against a series of other PERC profiles under consideration. Normally a patient PERC profile is set as the benchmark, but a transportation or destination PERC profile might be set as the benchmark under some conditions. In those situations, either the transportation or destination resource becomes the benchmark profile and is compared only to patient profiles of the patient cohort with the purpose of identifying the most appropriate patient recommended for that resource. For example, a pediatric hospital may be using the PERC system to match pediatric patients from multiple evacuating hospitals to accept to its different wards.

A benchmark value is the sum of positive characters (+) for the benchmark profile. Using table 2 as an example and setting individual i as the benchmark, the benchmark value would be 2.

When a benchmark PERC profile is compared to an individual PERC profile from a series (such as a series of patient, transportation resources, or destination resources), a match between the two PERC profiles results in a 1; a "no match results" in a 0, thus a match value is the sum of those results. Using Table 2 as an example, the match value for the two compared records is 1, because there was only 1 match.

TABLE 2

SCORES AND VALIDITY OF DICHOTOMOUS CHARACTER COMPARISONS

| | Values of character k | | | |
|---|---|---|---|---|
| Individual i | + | + | − | − |
| j | + | − | + | − |
| $s_{ijk}$ | 1 | 0 | 0 | 0 |
| $\delta_{ijk}$ | 1 | 1 | 1 | 0 |

Table 2 J. C. Gower Table Used to Calculate Scores and Validity of Dichotomous Character Comparisons. (Gower, 1971)

Finally, a response value is the sum of all areas of comparison with a positive character (+) for the two records or PERC profiles being considered. Using Table 2 (Gower) as an example once more, the combination value is 3, because the two records had positive characters in three areas of comparison.

Development of Safety and Efficiency Scoring

The PERC System has two separate analyses when comparing a patient PERC profile to the available transportation and destination resources; Adequacy and Efficiency. The adequacy analysis determines if the comparison matched a transportation or destination resource that at a minimum met all of the same attribute values reflected on a given patient PERC profile. The efficiency analysis determines how close to an exact match is discovered during that comparison and identifies the excess (or unused capabilities) for each resource considered. The adequacy analysis results in a Safety Score and the efficiency analysis results in an Efficiency Score.

Safety Scoring focuses on the adequacy of a given transportation or destination resource to ensure patient safety. In addition to the definition provided earlier, adequacy can also be defined as identifying a patient safe transportation or patient safe destination resource.

Quantitatively, patient safe transportation and destination resources Safety Scores are defined by the following algorithms:

$$\left[\frac{\sum_i f_i(x, t)}{\sum_i x_{(i,j)}}\right] \text{ or } \left[\frac{\sum_i f_i(x, d)}{\sum_i x(i, j)}\right] \text{ where } \sum_i f_i(x, t) \text{ and } \sum_i f_i(x, d)$$

sum of matches between a patient's resource needs and a destination resource capabilities (match value), and $$\sum_i x_{(i,j)}$$

represents the sum of patient's resource needs (benchmark value)

These algorithms express that in order for a transportation or destination resource to be adequate or patient safe, they each must meet (at a minimum) every patient resource need identified by the patient PERC profile, thus resulting in a Safety Score of 1.

Efficiency Scoring focuses on identifying the most efficient allocation option(s) for a given patient PERC profile. The algorithms developed for the efficiency scoring are designed to generate lower scores for assigned transportation or destination resources that have a large number of inherent resource capabilities that are not required by the patient's resource needs. It is note that algorithm is less processor-intensive and therefore improves the performance of the computer.

Patient Profile to Transportation Resource Profile—Efficiency Score $$S(x, t) = \left[\frac{\sum_i f_i(x, t)}{\sum_i \delta_{(i,j)}}\right] \text{ where } \sum_i f_i(x, t)$$

represent the sum of matches between a patient's resource needs and a transportation resource's capabilities (match value), and $$\sum_i \delta_{(i,j)}$$

represents the sum of all areas of comparison (response value)

Patient Profile to Destination Profile—Efficiency Score $$S(x, d) = \left[\frac{\sum_i f_i(x, d)}{\sum_i \delta_{(i,j)}}\right] \text{ where } \sum_i f_i(x, d)$$

represent the sum of matches between a patient's resource needs and a destination resource's capabilities (match value), and $$\sum_i \delta_{(i,j)}$$

represents the sum of all areas of comparison (response value)

To enhance decision support, the efficiency score ($S_{(i,j)}$) was developed to facilitate comparison between various transportation resource PERC profiles (creating S(x,t)) and/or various destination profiles (creating S(x,d)) for each patient PERC profile under consideration. The efficiency score is derived by taking either resource profile comparison score (S(x,t) & S(x,d)) and dividing it by the response values between the two compared profiles ($\delta_{(i,j)}$).

The flex resource expression may be used when some or none of a patient's resource needs are met by available transportation resource profiles and/or destination resource profiles. The use of a flex resource under these circumstances is referred to as an "upgrading option" which is discussed later. In most cases, the flex resource(s) available (and most qualified) are those that the patient was already using for ongoing care at the evacuating hospital. For example, an ICU nurse and a ventilator already in use in the care of the designated patient at the evacuating hospital may be allocated to create a patient-safe transportation resource (in some situations, flex transportation resources may return for reallocation), create a patient-safe destination (flex resources are allocated and no longer available to the remaining evacuation cases), or used for both transportation and destination resources.

Development of PERC Decision-Support Protocols

The PERC Decision-Support protocols are designed to accomplish objectives such as 1) evaluate and classify a transportation or destination resource for adequacy and 2) evaluate and rank each transportation or destination resource under consideration based on the efficiency of the match.

To achieve these two objectives, this disclosure may include up to six (6) sequential assessments for the two steps identified for PERC protocols. Step one has three assessments: 1) Classifying those resources that are patient safe, 2) Classifying resources that are potentially safe (i.e. resources that have the potential to be classified as patient safe if upgraded by the appropriate flex resources), and 3) Classifying available resources that are at-risk (i.e. resources that cannot be classified as patient safe due to the lack of an appropriate flex resource(s) and/or impeded by its design or structural limitations from an upgrade that meets a specific need). Step two also has three assessments: 1) For those resources that are patient safe, ranking them through their efficiency scores, 2) Ranking the potentially safe resources through their efficiency scores, and 3) Ranking the at-risk resources through their efficiency scores. The matching algorithm results are translated for decision-support classifications.

Classifying Resources as Patient Safe

As discussed previously, the Safety Scoring algorithms developed by this disclosure are used to quantitatively determine if a resource is patient safe, that resource or destination would have as a minimum a PERC profile that matches every patient resource need in the patient PERC profile. This 100% adequacy match is reflected quantitatively by a minimum safety score equal to 1.

$$\left[\frac{\sum_i f_i(x, t)}{\sum_i x_{(i,j)}}\right] = 1 \text{ or } \left[\frac{\sum_i f_i(x, d)}{\sum_i x_{(i,j)}}\right] = 1$$

For example, if the patient has seven (7) positive attribute values (7 yes answers) in their PERC profile reflecting the 7 patient resource needs, then all GREEN color on GUI (graphical user interface on computer 109) or patient safe transportation resource and destination resource profiles will have, as a minimum, the same seven (7) positive attribute values in their profile reflecting the equivalent resource capabilities.

Ranking Patient Safe Resources

Once a transportation or destination resource is qualified as patient safe, the Efficiency Score algorithms are used to rank all patient safe resources. An exact match without surplus capability would be represented by (S(x, t)=1), thus considered 100% efficient as explained in the efficiency scoring section.

Transportation or destination resource PERC profiles that meet all of the patient's PERC profile attribute types (thus considered patient safe), but significantly exceed the patient's resource needs (i.e., excess or unneeded capabilities) would receive a lower efficiency ranking than those with PERC profiles that exactly meet the needed capabilities (highest available efficiency). This prioritization approach is intended to help the decision-maker maximize the assignment of high value/low availability transportation or destination resources, such as a PCCT/ALS-B or Burn Ward/Neonatal ICU, to patients that do require all or most of those capabilities or levels of care.

Qualifying Resources as Potential

Resources that do not qualify as patient safe but do meet some of the positive patient attribute types AND can be upgraded by using available flex resources are qualified as potential resources and are represented visually as YELLOW on the GUI. These transportation or destination resources require expert judgment input by the decision-maker to be deemed "patient safe" for the matched patient profile. To assist with the decision process, the PERC Decision-Support Tool highlights those patient resource needs that are missing from the potential resource and incorporates an available flex resource code that could be used to meet that need. The PERC protocols then apply a new efficiency score to those newly upgraded patient safe resources based on the use of all recommended flex resources. They are then ranked accordingly.

Ranking Potential Resources

The PERC Decision-support Tool will display that resource's upgraded efficiency ranking if all of the required flex resources are assigned to make the resource patient safe.

Qualifying Resources as At-Risk

Resources that do not qualify as patient safe and cannot be upgraded by using available flex resources are designated as at-risk resources, and visually represented as RED on the GUI. These transportation or destination resources would only be considered if the risk to the patient remaining at the facility is greater than the risk of not meeting the patient medical needs represented by the missing attribute type that cannot be upgraded. To assist with the decision process, the PERC Decision-Support Tool highlights those patient attribute types that are missing and that can be upgraded in YELLOW on the GUI from the at-risk resource and inserts a flex resource code that could be used to meet that need. The PERC Decision-support Tool also highlights those patient resource needs that are missing but cannot be upgraded using available flex resources in RED on the GUI. The reason for an un-upgradeable designation for any given resource capability can be due to physical constraints, damage, or incompatibility issues with the resource under consideration or because there are no available flex resources to mitigate the missing attribute type.

Ranking At-Risk Resources

At-risk resources with the least un-upgradeable (having the fewest attributes that cannot be upgraded due to inherent design of the transportation resource) resource capabilities and with the least excess or unused capabilities would receive a higher efficiency ranking. The PERC Decision-Support Tool will also display each resources upgraded efficiency ranking if all of the required flex resources are assigned.

Example of Algorithms Applied Using PERC Protocols

Figure 13:
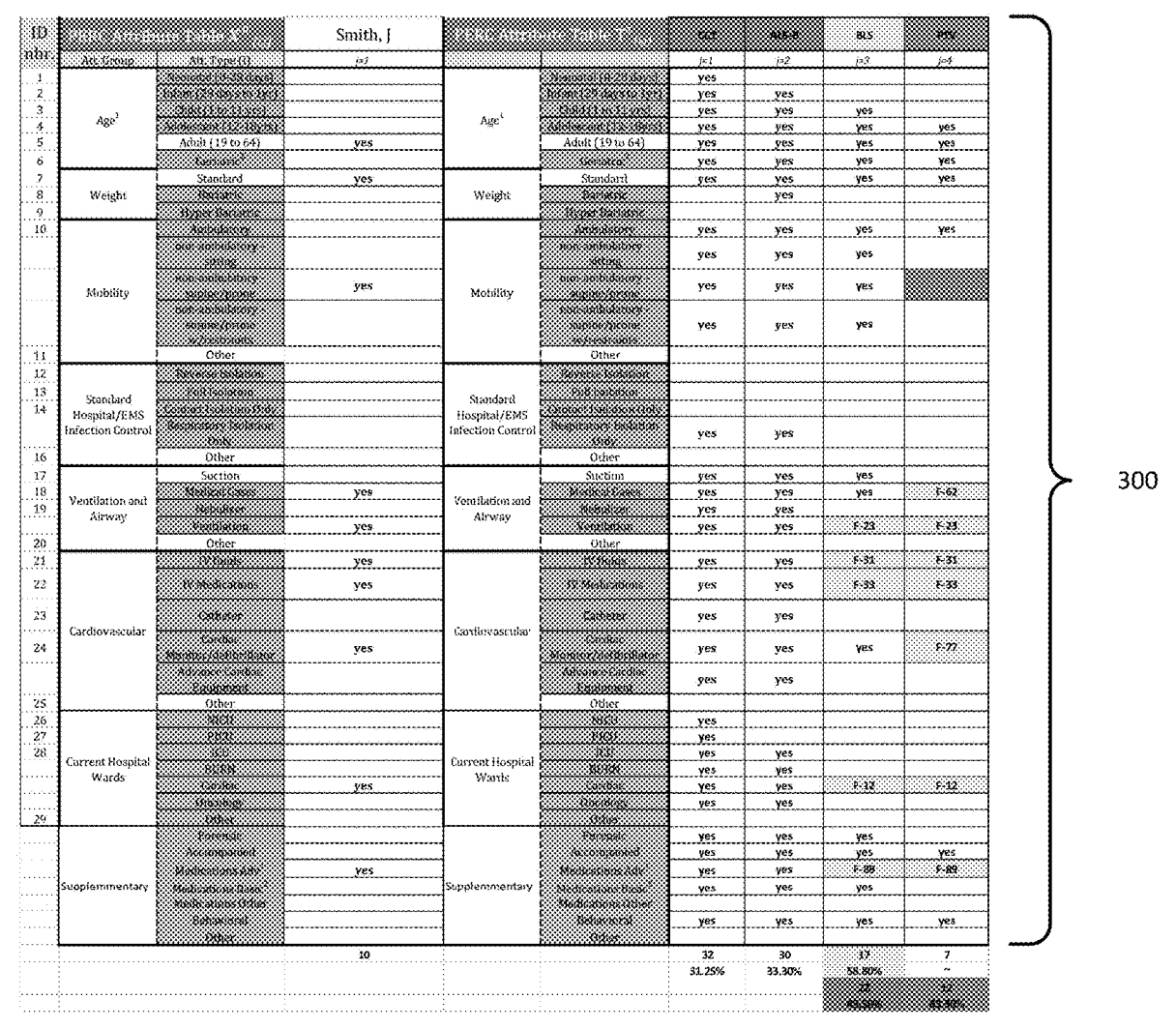

As displayed in FIG. 13, the patient selected for evacuation is Smith, J with the computer readable PERC profile 300 displayed on computer system. From this PERC profile 300, all medical personnel can see that Smith, J is an adult cardiac patient that requires a bed (supine), is on a ventilator supported by medical gases, requires an IV with fluids and medications, and needs those medications on the advanced formulary list.

The transportation resources available in the staging area to evacuate Smith, J include a Critical Care Truck (CCT), an Advanced Life Support Ambulance-Bariatric (ALS-B), a Basic Life Support Ambulance (BLS), and a Para-Transit Vehicle (PTV). The CCT and the ALS-B are considered patient safe transportation resource, but display very low efficiency rankings (31.25% and 33.30%) given the excess capabilities that will go unused if assigned to Smith, J. The BLS is considered a potential transportation resource and its missing patient attribute types are highlighted in YELLOW with a flex resource code inserted that indicates how to meet the relevant need. The upgraded BLS (all flex resources required have been assigned) has been made patient safe (subject to confirmation by the expert judgment of the decision-maker) and has an efficiency score of 45.5%. The PTV is considered an at-risk resource and its missing patient resource needs are highlighted in yellow as with the BLS, but highlights in RED the missing patient resource needs that cannot be upgraded.

Utilization—Development of Patient Cohort Evacuation Analysis

In addition to providing an efficiency ranking for each PERC profile comparison and capturing the efficiency ranking for each resource allocation, the PERC System also provides for two features, "utilization" guidance and post event scoring. The first utilization feature helps the decision makers gain level-3 situational awareness for each resource option under consideration (i.e., the ability to project forward to see the decision's impact on resource availability for remaining patients). The second feature, the overall utilization score, is available at the conclusion of the evacuation of the patient cohort it is comprised of the average efficiency ranking per allocation, and is produced for use during the after-action review process.

Using Flex Resources

If faced with no patient-safe or GREEN options or with only high value/low availability GREEN options, a decision maker may wish to use the recommended flex resources identified through the PERC profile comparison to upgrade a transportation or destination resource designated visually as a YELLOW or potential option to create a patient safe resource. For example, if an ALS transportation resource would normally be indicated if available, but none are available, then the selection of a BLS with the appropriate, PERC designated flex resources (nursing staff, equipment, and/or supplies) could create an upgraded option that would provide a patient safe transportation or destination resource for that patients PERC profile (subject to confirmation by the expert making the final decisions).

PERC System Concept of Operation and Benchmark Designation

The core concept of operation for the PERC process has the patients attributes (or patient's PERC profile) as the benchmark profile against which all available transportation resource and destination resource profiles are scanned for patient safe matches. It is assumed that, during a standard evacuation, patients are registered as available for transport upon checking into the patient staging area, which is in close proximity to the patient loading area. The available ambulances and other ground transport resources are registered (i.e., added to the transportation resource attribute table along with their pre-established transportation resource profile) as they arrive to a predetermined vehicle staging area to await a summons for patient loading. The evacuating hospital triage strategy identifies the priority patients for evacuation; as each arrives in patient staging, his or her patient profile is compared against the available transportation resource and destination resource profiles. Best available matches for that patient are considered and then the transportation resource and destination resource are allocated. The algorithms in the decision-support tool are designed to consider both adequacy (patient-safety) and efficiency (avoiding the matching of scarce resources to a patient that would be safe with a less capable resource) in presenting matched options, so that the number of patients transported in adequate resources and to adequate destinations will be optimized across the evacuee population. This is a decision support tool, so the final selections are confirmed by the designated expert supervising this resource allocation process.

In some extreme emergency evacuation situations, patients must be moved very quickly and the major constraint is transportation resources. In these emergencies, the driving (benchmark) profile may be the PERC profile of an arriving transportation resource rather than the next patient PERC profile from the patient staging area. In this circumstance, the benchmark designation would be given to the transportation resource PERC profile selected as the starting point for the analysis. This approach presents the match of patient profiles already available in the staging area (and/or the entire patient cohort) for which this transportation resource would be patient-safe and also list those patients for which this transportation resource would be a potential transportation resource given the assignment of the appropriate flex resources.

This benchmark flexibility is also applied during standard patient evacuations as a secondary feature, which facilitates the decision-maker's ability to project beyond the individual patient to increase transportation fleet utilization and destination resource utilization. During the resource selection process, the decision maker can select a resource being considered and then initiate the secondary feature (right click) to see a pop up list of on the graphical user interface of patients ranked for that particular resource. At this point, the decision-maker can determine how the patient under consideration is ranked for the resource and determine if the selection would be appropriate, noting the impact on the greater patient cohort.

Model Assessment

As a part of the model assessment and use of expert judgment to prepare for the simulation, this disclosure uses a Convergence Interview approach. This process achieved saturation after five interviews. As a consequence of the CI method, the PERC prototype was revised as follows:

The following attributes were recommended for inclusion in the PERC System table: Chest Tubes, Tube Feeding, Foley Catheter, and Catheter.

The following Destination attribute was recommended for inclusion in the PERC system table: Step Down (Intermediate Care) Unit, as an option between critical care units and regular inpatient units.

The interview process also captured recommendations to revise patient evacuation forms (both Harvard and HICS). These recommendations included:

Revising the patient profiles and evacuation forms for patient j=1 (Bariatric Patient) changing the Mobility value from "non-ambulatory—supine/prone" to "non-ambulatory supine/prone w/restraints", and changing the primary diagnosis or primary medical condition for Patient B=1 to "Pulmonary Embolism" from "Hypoglycemic coma with 2° brain injury" to create a more equitable duplicate to A=1 (One week s/p posterior circulation CVA-stroke due to AFIB.

Revising the patient profiles and evacuation forms for patient j=2 (Pediatric/Neonatal ICU Patient) changing the primary diagnosis or primary medical condition for Patient B=1 to "Premature birth (30 weeks) with respiratory failure due to pneumonia" from "Premature birth (30 weeks) with respiratory distress syndrome since birth" to create a more equitable duplicate to A=2 (Early Onset Neonatal Sepsis).

Revising the patient profiles and evacuation forms for patient j=4 (Cardiac Patient) adding "Basic Medications".

Revising the patient profiles and evacuation forms for patient j=5 (Oncology Patient) adding "IV fluids" and "IV Medications".

Revising the patient profiles and evacuation forms for patient j=7 (Infectious Disease Patient) clarifying and adding "Contact Isolation" and "Airborne/Droplet Isolation".

Revising the patient profiles and evacuation forms for patient j=8 (Ventilator Patient) adding "Chest Tube".

Revising the patient profiles and evacuation forms for patient j=9 (Geriatric—DNR Patient) adding "Ventilation" and "Foley Catheter"

The interview process provided recommendations and guidance for potential research, which are addressed in the foregoing.

Proof of Concept Through Solomon Four-Group Simulation Results

Data collected for the Session 1 was exported using Excel and the data for the second session was exported in a Word format. Before a direct comparison of the data was possible, the Session 1 Excel report was manually translated into the PERC format. This PERC table was designed so, as the observations were applied, the calculated data elements were created using the appropriate formulas. For example, the mean for the individual patient allocation times ($\bar{t}_{\alpha_1}$), was automatically calculated by gathering the sum of each patient allocation and then dividing by the number of patients. Another example is the calculation of the various Utilization Parameters (Transportation, Destination, and Event) by taking the sum of each respective allocation efficiency and dividing them by the number of allocations. The observational results designed to address the proof of concept hypotheses addressed in Appendix and in detail in the following section on Quantitative Analysis.

Quantitative Analysis of the Simulation Design and Observations

Once all of the data elements had been identified, they were grouped, tested for normality, and tested for statistical significance. The first set of tests used a significance level (a) of 5% or 0.05. This significance resulted in mixed results as explained in the next section. The next set of tests used a significance level (a) of 10% or 0.1.

Normality Testing

The first data set tested was the Prototype Time Observations—Session 2 ($t_{\alpha_2}$) selected for a design test for internal validity. Using Minitab, the following data was tested for normality; Group 1 and Group 2 in Session 2 ($G_1P_{2A}$ and $G_2P_{2B}$) and Groups 3 and 4 from Session 2 sets (GPA and $G_4P_{2B}$). This data is displayed in Table 5-4.

TABLE 5-4

Prototype Time Observations

| $t_{\alpha 2}$ | G1-P2A & G2-P2B | X-MEAN | (X-MEAN)$^2$ | G3-P2A & G4-P2B | X-MEAN | (X-MEAN)$^2$ |
|---|---|---|---|---|---|---|
|  | 4.08 | 1.80 | 3.25 | 2.00 | 0.72 | 0.51 |
|  | 4.02 | 1.74 | 3.03 | 0.95 | −0.33 | 0.11 |
|  | 2.70 | 0.42 | 0.18 | 1.45 | 0.17 | 0.03 |
|  | 1.27 | −1.01 | 1.02 | 0.73 | −0.55 | 0.31 |
|  | 0.62 | −1.66 | 0.12 |  |  |  |
|  | 0.98 | −1.30 | 1.69 |  |  |  |
| Sum | 13.67 | 0.00 | 9.28 | 5.13 | 0.00 | 0.96 |
| Mean | 2.28 |  |  | 1.28 |  |  |

$H_0$: The sampled population is normally distributed
$H_1$: The sampled population is not normally distributed
Using the Anderson-Darling Normality Test feature in Minitab under the Basic Statistics Option, the following graph and report FIG. 14 was created.

At $\alpha(0.05)$ with a p value of 0.055, the research is unable to reject the null. Thus the data is considered to be normally distributed. However, at $\alpha(0.10)$ with a p value of 0.55, the research rejects the null. Thus, the data is NOT considered to be normally distributed.

The second data set tested was the Prototype Efficiency Observations rototype Ef ($U_{v_2}$) also a data set for a design test on internal validity. Using Minitab, the following data was tested for normality; Group 1 and Group 2 in Session 2 sets ($G_1P_{2A}$ and $G_2P_{2B}$) and Group 3 and Group 4 in Session 2 sets ($G_3P_{2A}$ and $G_4P_{2B}$). This data is displayed in Table 5-5.

TABLE 5-5

Prototype Efficiency Observations

| $U_{v2}$ | G1-P2A & G2-P2B | X-MEAN | (X-MEAN)$^2$ | G3-P2A & G4-P2B | X-MEAN | (X-MEAN)$^2$ |
|---|---|---|---|---|---|---|
|  | 45.96 | 4.05 | 16.43 | 34.78 | −6.81 | 46.38 |
|  | 36.52 | −5.39 | 29.02 | 44.00 | 2.41 | 5.81 |
|  | 40.38 | −1.53 | 2.33 | 43.61 | 2.02 | 4.08 |
|  | 45.75 | 3.84 | 14.77 | 43.97 | 2.38 | 5.66 |
|  | 45.44 | 3.53 | 0.12 |  |  |  |
|  | 37.39 | −4.52 | 20.40 |  |  |  |
| SUM | 251.44 | 0.00 | 83.07 | 166.36 | 0.00 | 61.93 |
| MEAN | 41.91 |  |  | 41.59 |  |  |

$H_0$: The sampled population is normally distributed
$H_1$: The sampled population is not normally distributed Using the Anderson-Darling Normality Test feature in Minitab under the Basic Statistics Option, the graph and report was created in FIG. 15.

Given that the P Value is greater than $\alpha(0.05)$, the research is unable to reject the null. Thus the data is considered to be normally distributed. However, at $\alpha(0.1)$ the research rejects the null and the data are considered NOT normally distributed.

The third data set tested was the Prototype Event Utilization Observations—($U_{v_1}$ & $U_{v_2}$) selected for an interval validity test for causality and randomization. Using Minitab, the following data was tested for normality; Group 1, Group 2, and Group 3 with Patient A Files sets ($G_1P_{2A}$, $G_2P_{1A}$, and $G_3P_{2A}$) and Group 1, Group 2, and Group 4 with Patient B Files sets ($G_1P_{1B}$, $G_2P_{2B}$, and $G_4P_{2B}$). This data is displayed in Table 5-6.

TABLE 5-6

Prototype Event Utilization Observations

| EVENT UTILIZATION | G1 | G2 | G3 | G4 | |
|---|---|---|---|---|---|
| Patient A Files | 18.06 | 45.75 | | | |
| | 7.64 | 45.44 | 43.61 | | Set A Mean |
| | 16.28 | 37.39 | 43.97 | | 32.27 |
| A Group Means | 13.99 | 42.86 | 43.79 | | |
| Patient B Files | 45.96 | 6.31 | | | |
| | 36.52 | 0.00 | | 34.78 | Set B Mean |
| | 40.38 | 0.00 | | 44.00 | 25.99 |
| B Group Means | 40.95 | 2.10 | | 39.39 | |
| SUM | 178.83 | 177.75 | 87.58 | 78.78 | TOTAL AVERAGE |
| MEAN | 27.47 | 22.48 | 43.79 | 39.39 | 29.13 |

$H_0$: The sampled population is normally distributed
$H_1$: The sampled population is not normally distributed Using the Anderson-Darling Normality Test feature in Minitab under the Basic Statistics Option, the graph and report was created shown in FIG. 16.

Given that the P Value is less than $\alpha(0.05)$, the research rejects the null. Thus, the data is considered to NOT be normally distributed. Testing at $\alpha(0.1)$ was not necessary.

In order to determine if this data set could still be used for ANOVA testing, it was tested to see if the residuals for each factor were normally distributed. The following null and alternative hypotheses were generated:

$H_0$: The residuals for the sampled population are normally distributed
$H_1$: The residuals for the sampled population are not normally distributed The first factor residual test, Patient Files, produced the results shown in FIGS. 17 and 18.

Given that the P Value is less than $\alpha(0.05)$, the research rejects the null. Thus the residuals are considered to NOT be normally distributed. Testing at $\alpha(0.1)$ was not necessary.

As the residuals are not normally distributed, the ANOVA test intended for this statistical analysis was not possible.

The second factor residual test, Group Assignment, produced the following results shown in FIG. 19.

With a high P Value $(0.439) > \alpha(0.05)$ and $\alpha(0.1)$, the regression analysis shows that changes in Group Assignment are NOT associated with changes to the observations for Event Utilization. These results are discussed further in the statistical analysis of the simulation design. With the stored standardized residuals (SRES2), the research conducted a normality test with the following results shown in FIG. 20.

Given that the P Value is less than $\alpha(0.05)$, the research rejects the null. Thus the residuals are considered to NOT be normally distributed. Testing at $\alpha(0.1)$ was not necessary.

As the residuals are not normally distributed, the ANOVA test intended for this statistical analysis is not possible.

The next data set tested was the Time Observations—Session 1 ($t_{\alpha_1}$) and Session 2 ($t_{\alpha_2}$) and is the first data set for research hypothesis testing, specifically for Research Question #3. Using Minitab, the following data was tested for normality; Group 1 and Group 2 in Session 1 sets ($G_1P_{1B}$ and $G_2P_{1A}$) and Group 1 and Group 2 in Session 2 sets ($G_1P_{2A}$ and $G_2P_{2B}$). This data is displayed in Table 5-7. See FIG. 14.

TABLE 5-7

Time Observations (Session 1 and Session 2)

| PANEL MEMBER | $\bar{t}_{\alpha_1}$ TIME ALLOCATION (Session 1) | $\bar{t}_{\alpha_2}$ TIME ALLOCATION (Session 2) | | Δ | Δ^2 | |
|---|---|---|---|---|---|---|
| G1-1 | 4.52 | 0.82 | | -3.7 | 13.7 | |
| G1-2 | 3.83 | 2.45 | | -1.4 | 1.90 | |
| G1-3 | 3.68 | 1.32 | | -2.4 | 5.57 | |
| G2-1 | 4.08 | 1.27 | | -2.8 | 7.90 | CALC |
| G2-2 | 4.02 | 0.62 | | -3.4 | 11.6 | STD |
| G2-3 | 2.7 | 0.98 | | -1.7 | 2.96 | DEV |
| SUM | 22.83 | 7.46 | SUM | -15 | 43.6 | 236.2 | 0.9171 |
| MEAN | 3.805 | 1.24 | MEAN | -2.6 | | | |
| | | STD DEV | | 0.92 | | |

$H_0$: The sampled population is normally distributed
$H_1$: The sampled population is not normally distributed Using the Anderson-Darling Normality Test feature in Minitab under the Basic Statistics Option, the graph and report shown in FIG. 21 was created.

Given that the p value is greater than $\alpha(0.05)$, the research is unable to reject the null. Thus the data is considered to be normally distributed. At $\alpha(0.1)$ the p value is less, rejecting the null and the data is considered NOT normally distributed.

The next data set tested was the Transportation Efficiency Observations—Session 1 ($U_{k_1}$) and Session 2 ($U_{k_2}$) chosen to test the associated hypotheses with Research Question #2. Using Minitab software, the following data was tested for normality; Group 1 and Group 2 in Session 1 sets ($G_1P_{1B}$ and $G_2P_{1A}$) and Group 1 and Group 2 in Session 2 sets ($G_1P_{2A}$ and $G_2P_{2B}$). This data is displayed in Table 5-8.

TABLE 5-8

Transportation Efficiency Observations

| PANEL MEMBER | $U_{k_1}$ Transportation Efficiency (Session 1) | $U_{k_2}$ Transportation Efficiency (Session 2) | | Δ | Δ^2 | | | |
|---|---|---|---|---|---|---|---|---|
| G1-1 | 24.06 | 47.16 | | 23.1 | 533.61 | | | |
| G1-2 | 10.28 | 36.4 | | 26.1 | 682.25 | | | |
| G1-3 | 21.85 | 41.05 | | 19.2 | 368.64 | | | |
| G2-1 | 8.28 | 46.74 | | 38.5 | 1479.17 | | CALC | |
| G2-2 | 0 | 46.73 | | 46.7 | 2183.69 | | STD | |
| G2-3 | 0 | 37.41 | | 37.4 | 1399.51 | | DEV | |
| SUM | 64.47 | 255.49 | SUM | 191 | 6646.88 | 36488.6 | 10.634 | |
| MEAN | 10.745 | 42.58 | MEAN | 31.8 | | | | |
| | | STD DEV | | 10.6 | | | | |

$H_0$: The sampled population is normally distributed
$H_1$: The sampled population is not normally distributed Using the Anderson-Darling Normality Test feature in Minitab under the Basic Statistics Option, the graph and report shown in FIG. 22 was created.

Given that the p value is greater than α(0.05), the research is unable to reject the null. Thus the data is considered to be normally distributed. At α(0.1) the p value is less, thus rejecting the null and the data is considered NOT normally distributed.

The next data set tested was the Destination Efficiency Observations—Session 1 ($U_{d_1}$) and Session 2 ($U_{d_2}$) to address the associated hypotheses with Research Question #2. Using Minitab, the following data was tested for normality; Group 1 and Group 2 in Session 1 sets ($G_1P_{1B}$ and $G_2P_{1A}$) and Group 1 and Group 2 in Session 2 sets ($G_1P_{2A}$ and $G_2P_{2B}$). This data is displayed in Table 5-9.

TABLE 5-9

Destination Efficiency Observations

| PANEL MEMBER | $U_{d_1}$ Destination Efficiency (Session 1) | $U_{d_2}$ Destination Efficiency (Session 2) | | Δ | Δ^2 | | | |
|---|---|---|---|---|---|---|---|---|
| G1-1 | 12.07 | 47.16 | | 35.1 | 1231.31 | | | |
| G1-2 | 5 | 36.64 | | 31.6 | 1001.09 | | | |
| G1-3 | 10.71 | 39.71 | | 29 | 841.00 | | | |
| G2-1 | 4.33 | 44.76 | | 40.4 | 1634.58 | | | |
| G2-2 | 0 | 44.15 | | 44.2 | 1949.22 | | CALC | |
| G2-3 | 0 | 37.38 | | 37.4 | 1397.26 | | STD DEV | |
| SUM | 32.11 | 249.8 | SUM | 218 | 8054.47 | 47389 | 5.6 | |
| MEAN | 5.35 | 41.63 | MEAN | 36.3 | | | | |
| | | STD DEV | | 5.59 | | | | |

$H_0$: The sampled population is normally distributed
$H_1$: The sampled population is not normally distributed Using the Anderson-Darling Normality Test feature in Minitab under the Basic Statistics Option, the graph and report shown in FIG. 23 was created.

Given that the P Value is less than α(0.05), the research rejects the null. Thus the data is considered to NOT be normally distributed. Testing at α(0.1) was not necessary.

The next data set tested was the Patient Safe Observations—Session 1 ($PS_1$) and Session 2 ($PS_2$) developed to address Research Question #3. Using Minitab, the following data was tested for normality; Group 1 and Group 2 in

TABLE 5-10

Patient Safe Observations

| PANEL MEMBER | $PS_1$ Patient Safe Evacuations (Session 1) | $PS_2$ Patient Safe Evacuations (Session 2) | Δ | Δ^2 | |
|---|---|---|---|---|---|
| G1-1 | 4 | 10 | 6 | 36.00 | |
| G1-2 | 2 | 8 | 6 | 36.00 | |
| G1-3 | 3 | 9 | 6 | 36.00 | |
| G2-1 | 1 | 10 | 9 | 81.00 | CALC |

TABLE 5-10-continued

Patient Safe Observations

| PANEL MEMBER | $PS_1$ Patient Safe Evacuations (Session 1) | $PS_2$ Patient Safe Evacuations (Session 2) | | Δ | Δ^2 | | |
|---|---|---|---|---|---|---|---|
| G2-2 | 0 | 9 | | 9 | 81.00 | | STD |
| G2-3 | 0 | 9 | | 9 | 81.00 | | DEV |
| SUM | 10.00 | 55.00 | SUM | 45 | 351 | 2025 | 1.6 |
| MEAN | 1.67 | 9.17 | MEAN | 7.5 | | | |
| | | STD DEV | | 1.64 | | | |

$H_0$: The sampled population is normally distributed
$H_1$: The sampled population is not normally distributed Using the Anderson-Darling Normality Test feature in Minitab under the Basic Statistics Option, the graph and report shown in FIG. 24 was created.

Given that the P Value is less than $\alpha(0.05)$, the research rejects the null. Thus, the data is considered to NOT be normally distributed. Testing at $\alpha(0.1)$ was not necessary.

The final data set tested was the Event Utilization Observations—Session 1 $U_{v_1}$ and Session 2 $U_{v_2}$ chosen to address associated hypotheses for Research Question #3. Using Minitab, the following data was tested for normality; Group 1 and Group 2 in Session 1 sets ($G_1P_{1B}$ and $G_2P_{1A}$) and Group 1 and Group 2 in Session 2 sets ($G_1P_{2A}$ and $G_2P_{2B}$). This data is displayed in Table 5-11.

TABLE 5-11

Event Utilization Observations

| PANEL MEMBER | $U_{v_1}$ Event Utilization (Session 1) | $U_{v_2}$ Event Utilization (Session 2) | | $\Delta$ | $\Delta^2$ | | |
| --- | --- | --- | --- | --- | --- | --- | --- |
| G1-1 | 18.06 | 45.96 | | 27.9 | 778.4 | | |
| G1-2 | 7.64 | 36.52 | | 28.9 | 834 | | |
| G1-3 | 16.28 | 40.38 | | 24.1 | 580.8 | | |
| G2-1 | 6.31 | 45.75 | | 39.4 | 1555 | | CALC |
| G2-2 | 0 | 45.44 | | 45.4 | 2064 | | STD |
| G2-3 | 0 | 37.39 | | 37.4 | 1398 | | DEV |
| SUM | 48.29 | 251.44 | SUM | 203 | 7211 | 41270 | 8.16 |
| MEAN | 8.05 | 41.91 | MEAN | 33.9 | | | |
| | | | STD DEV | 8.16 | | | |

$H_0$: The sampled population is normally distributed
$H_1$: The sampled population is not normally distributed Using the Anderson-Darling Normality Test feature in Minitab under the Basic Statistics Option, the graph and report shown in FIG. 25 was created.

Given that the P Value is greater than $\alpha(0.05)$, the research is unable to reject the null. Thus, the data is considered to be normally distributed. At $\alpha(0.1)$ the p value is less, thus rejecting the null and the data is considered NOT normally distributed.

TABLE 5-12

Summary of Normality Tests Results
Summary of Normality Tests Results

| Data Set | Design/ Prototype | Test Used | Results $\alpha(0.05)$ | Results $\alpha(0.1)$ |
| --- | --- | --- | --- | --- |
| Time Parameter- Session 2 ($t_{\alpha_2}$). | Design | Anderson- Darling | Normally Distributed | NOT |
| Event Utilization - Session 2 ($U_{v_2}$) | Design | Anderson- Darling | Normally Distributed | NOT |
| Event Utilization - All Observations ($U_{v_1}$ & $U_{v_2}$) | Design | Anderson- Darling | NOT Normally Distributed | N/A |
| Event Utilization - All Observations ($U_{v_1}$ & $U_{v_2}$) Patient Files Residuals | Design | Anderson- Darling | NOT Normally Distributed | N/A |
| Event Utilization - All Observations ($U_{v_1}$ & $U_{v_2}$) Group Assignment Residuals | Design | Anderson- Darling | NOT Normally Distributed | N/A |
| Time Parameter - All Observations ($t_{\alpha_1}$ & $t_{\alpha_2}$) | Prototype | Anderson- Darling | Normally Distributed | NOT |
| Utilization Transportation Parameter - Group 1 and Group 2 ($U_{k_1}$ & $U_{k_2}$) | Prototype | Anderson- Darling | Normally Distributed | NOT |

TABLE 5-12-continued

Summary of Normality Tests Results
Summary of Normality Tests Results

| Data Set | Design/ Prototype | Test Used | Results $\alpha(0.05)$ | Results $\alpha(0.1)$ |
| --- | --- | --- | --- | --- |
| Utilization Destination Parameter - Group 1 and Group 2 ($U_{d_1}$ & $U_{d_2}$) | Prototype | Anderson- Darling | NOT Normally Distributed | N/A |
| Patient Safe - Group 1 and Group 2 ($PS_1$ & $PS_2$) | Prototype | Anderson- Darling | NOT Normally Distributed | N/A |

TABLE 5-12-continued

Summary of Normality Tests Results
Summary of Normality Tests Results

| Data Set | Design/ Prototype | Test Used | Results $\alpha(0.05)$ | Results $\alpha(0.1)$ |
| --- | --- | --- | --- | --- |
| Event Utilization Parameter - Group 1 and Group 2 ($U_{v_1}$ & $U_{v_2}$) | Prototype | Anderson- Darling | Normally Distributed | NOT |

Statistical Significance Testing

The statistical analysis for the observations related to simulation design and prototype used ANOVA and dependent t-test analysis for those data sets that were normally distributed. Wilcoxon and regression analysis were used for those data sets not normally distributed.

Design Testing:

The Solomon Four-Group methodology was selected for the statistical testing because it addresses validity concerns with the simulation design. This test was conducted at both $\alpha(0.05)$ using T-test and $\alpha(0.1)$ using Mann—Whitney.

Internal Validity Due to Method: A concern with Session 1 and Session 2 design is the potential for a Session 1 "pretest sensitization" effect (Sawilowsky, Kelley, Blair, & Markman, 2015, p. 364). To test for this internal validity concern, a comparison was made using observations from Session 2 for Group 1 and Group 2 ($G_1P_{2A}$ and $G_2P_{2B}$) and observations from Group 3 and Group 4 for Session 2 ($G_3P_{2A}$ and $G_4P_{2B}$). To conduct this test the following null hypothesis was developed:

$H_0$=Session 1 participation had no significant effect on prototype observations noted during Session 2

Two data elements for each data set were selected, Prototype Time Observations—Session 2 ($t_{\alpha_2}$) and Event Utilization Observations—Session 2 ($U_{v_2}$).

The first data element test (Prototype Time Observations) used a two sample T-Test. FIG. 25 shows that P-Value is 0.199, which is greater than $\alpha(0.05)$. Thus the research is unable to reject the null. Therefore, there was NO pretest sensitization noted for Session 1 participation using Prototype Time Observations from Session 2.

At $\alpha(0.01)$ this data set was not normally distributed, so the nonparametric two-sample t-test equivalent, Mann-Whitney was used. FIG. 26 shows that P-Value is 0.4555, which is greater than $\alpha(0.1)$. Thus the research is unable to reject the null. Therefore, there was NO pretest sensitization noted for Session 1 participation using Prototype Time Observations from Session 2.

The second data element test (Event Utilization Observations) was conducted at both $\alpha(0.05)$ using T-test and $\alpha(0.1)$ using Mann-Whitney. FIG. 27 shows that P-Value is 0.319, which is greater than $\alpha(0.05)$. Thus the research is unable to reject the null. Therefore, there was NO pretest sensitization noted for Session 1 participation using Event Utilization Observations from Session 2.

At $\alpha(0.01)$ this data set was not normally distributed, so the nonparametric two-sample t-test equivalent, Mann-Whitney was used. FIG. 28 shows that P-Value is 0.2410, which is greater than $\alpha(0.1)$. Thus the research was unable to reject the null. Therefore, there was NO pretest sensitization noted for Session 1 participation using Prototype Time Observations from Session 2.

As both sets of tests results indicated that Session 1 had no effect on Session 2 observations, the research is able to conclude that no pretest sensitization could be identified.

Causality and Randomization Due to Design: To determine possible influence by external and internal factors caused by the panel design, the Solomon Four-Group design allows for tests between those groups using different sets of tools or simulation-generated data and for randomization of panel member group assignment (Stambler K. S., 2015). In the case of this simulation, a test for causality was performed to measure any possible influence by the two sets of patient files created for panel members—patient files A or RED ($G_1P_{2A}$, $G_2P_{1A}$, and $G_3P_{2A}$) and patient files B or BLUE ($G_1P_{1B}$, $G_2P_{2B}$, and $G_4P_{2B}$). The same test would check for any significant effect caused by the random panel member assignment. To conduct this test, the following null hypotheses were created:

$H_0$=Patient Files had no significant effect on observations
$H_0$=Group assignment had no significant effect on observations Two sets of observations for each factor analysis were selected; Event Utilization Observations from Session 1 and Session 2 ($U_{v_1}$ & $U_{v_2}$)

A Two-Way ANOVA was originally proposed for this test, however, since the data sets for Event Utilization Observations for Group 1 and Group 2 and their respective residuals were not normally distributed, each factor was tested independently using Minitab's general linear regression tool. FIG. 27 displays the statistical analysis for the first factor (Patient Files). As noted during the residual normality test, the P-Value of 0.499 is greater than $\alpha(0.05)$. Thus the research noted that changes in the Patient Files were not associated with changes to the Event Utilization Observations.

FIG. 28 displays the statistical analysis for the second factor (Group Assignment). As noted during the residual normality test, the P-Value of 0.439 is greater than $\alpha(0.05)$. Thus the research noted that Group Assignment did not indicate an association with changes to the Event Utilization Observations.

Given that both factor tests indicated no association with Event Utilization Observations, it be can concluded that there were no causality or randomization issues with the simulation design.

Prototype Testing

Since there were no noted design issues, the research was able to use the simulation observations to determine if the PERC Decision-Support Tool (PERC Prototype) had any significant effect on the observations. This analysis focused on the observations shown in Table 5-12 for Group 1 and Group 2 (Session 1 and Session 2) with the relevant null hypothesis. These test were conducted at both $\alpha(0.05)$ using T-test and $\alpha(0.1)$ using Wilcoxon.

TABLE 5-13

Prototype Testing Hypotheses $\bar{t}_{\alpha_1}$ - Time parameter patient allocation (Session 1)    $\bar{t}_{\alpha_2}$ - Time parameter patient allocation (Session 2)
$H_0$ = PERCS had no significant effect on patient allocation time observations
$\bar{t}_{\alpha_2} = \bar{t}_{\alpha_1}$
$H_1$ = PERCS improved patient allocation time observations $\bar{t}_{\alpha_2} < \bar{t}_{\alpha_1}$ $U_{k_1}$ - Utilization parameter transportation (Session 1)    $U_{k_2}$ - Utilization parameter transportation (Session 2)
$H_0$ = PERCS had no significant effect on utilization transportation efficiency observations
$U_{k_2} = U_{k_1}$
$H_1$ = PERCS improved utilization transportation efficiency observations
$U_{k_2} > U_{k_1}$ $U_{d_1}$ - Utilization parameter destination (Session 1)    $U_{d_2}$ - Utilization parameter destination (Session 2)
$H_0$ = PERCS had no significant effect on utilization destination efficiency observations
$U_{d_2} = U_{d_1}$
$H_1$ = PERCS improved utilization destination efficiency observations
$U_{d_2} > U_{d_1}$ $PS_1$ - Patient Safe Evacuation (Session 1)    $PS_2$ - Patient Safe Evacuation (Session 2)
$H_0$ = PERCS had no significant effect Patient Safe Evacuations $PS_2 = PS_1$
$H_1$ = PERCS increased Patient Safe Evacuations $PS_2 > PS_1$ $U_{v_1}$ - Event utilization parameter (Session 1)    $U_{v_2}$ - Event utilization parameter (Session 2)
$H_0$ = PERCS had no significant effect on event utilization observations $\bar{U}_{v_2} = \bar{U}_{v_1}$
$H_1$ = PERCS improved event utilization observations $\bar{U}_{v_2} > \bar{U}_{v_1}$ A dependent (paired) T-Test was used with the first set of observations used (Time Parameter). FIG. 31 displays the test results and the data for Group 1 and Group 2-Session 1 in column C1 and for Group 1 and Group 2-Session 2 in column C2.

With a p value of 0.001 at $\alpha(0.05)$, the research rejects the null. Thus, the alternative hypothesis that the PERC System improved patient allocation time observations is supported.

Since this data set was not normally distributed at $\alpha(0.1)$, A Wilcoxon test was used with the first set of observations used (Time Parameter). FIG. 32 displays the test results and the data for Group 1 and Group 2-Session 1 in column C1 and for Group 1 and Group 2-Session 2 in column C2.

With a p-value of 0.036 at $\alpha(0.1)$, the research rejects the null. Thus, the alternative hypothesis that the PERC System improved patient allocation time observations is supported.

TABLE 5-14

Time Parameter Hypothesis Results $\bar{t}_{\alpha_1}$ - Time parameter patient allocation (Session 1)   $\bar{t}_{\alpha_2}$ - Time parameter patient allocation (Session 2)
$H_0$ = PERCS had no significant on patient allocation time observations effect
$\bar{t}_{\alpha_2} = \bar{t}_{\alpha_1}$ A dependent (paired) T-Test was used with the second set of observation (Utilization Parameter—Transportation). FIG. 30 displays the test results and the data for Group 1 and Group 2-Session 1 in column C1 and for Group 1 and Group 2-Session 2 in column C2.

With a p value of 0.001 at $\alpha(0.05)$, the research rejects the null. Thus, the alternative hypothesis that the PERC System improved transportation efficiency observations is supported. Since this data set was not normally distributed at $\alpha(0.1)$, A Wilcoxon test was used with the first set of observations (Utilization Parameter-Transportation). FIG. 34 displays the test results and the data for Group 1 and Group 2-Session 1 in column C1 and for Group 1 and Group 2-Session 2 in column C2.

With a p-value of 0.036 at $\alpha(0.1)$, the research rejects the null. Thus, the alternative hypothesis that the PERC System improved transportation efficiency observations is supported.

TABLE 5-15

Event Utilization (Transporation) Hypothesis Results $U_{k_1}$ - Utilization parameter transportation (Session 1)   $U_{k_2}$ - Utilization paramerter transportation (Session 2)
$H_0$ = PERCS had no significant effect on utilization transportation efficiency observations
$U_{k_2} = U_{k_1}$
$H_1$ = PERCS improved utilization transportation efficiency observations
$U_{k_2} > U_{k_1}$ A Wilcoxon Signed Rank Test was used with the third set of observations (Utilization Parameter-Destination). FIG. 31 displays the test results and the data for Group 1 and Group 2-Session 1 in column C1 and for Group 1 and Group 2-Session 2 in column C2.

With a P-Value of 0.036 at $\alpha(0.05)$ and $\alpha(0.1)$, the research rejects the null. Thus, the alternative hypothesis that the PERC System improved destination efficiency observations is supported.

TABLE 5-16

Event Utilization (Destination) Hypothesis Results $U_{d_1}$ - Efficiency parameter destination (Session 1)   $U_{d_2}$ - Efficiency paramerter destination (Session 2)
$H_0$ = PERCS had no significant effect on utilization destination efficiency observations
$U_{d_2} = U_{d_1}$
$H_1$ = PERCS improved utilization destination efficiency observations
$U_{d_2} > U_{d_1}$ A Wilcoxon Signed Rank Test was used with the fourth data element used (Patient Safe Evacuation). FIG. 32 displays the test results and the data for Group 1 and Group 2-Session 1 in column C1 and for Group 1 and Group 2-Session 2 in column C2.

With a P-Value of 0.036 at $\alpha(0.05)$ and $\alpha(0.1)$, the research rejects the null. Thus, the alternative hypothesis that the PERC System improved Patient Safe Evacuation observations is supported.

TABLE 5-17

Patient Safe Evacuation Hypothesis Results $PS_1$ - Patient Safe Evacuation (Session 1)   $PS_2$ - Patient Safe Evacuation (Session 2)
$H_1$ = PERCS increased Patient Safe Evacuations $PS_2 = PS_1$
$H_1$ = PERCS increased Patient Safe Evacuations $PS_2 > PS_1$ A dependent (paired) T-Test was used with the final set of observations (Event Utilization Parameter). FIG. 33 displays the test results and the data for Group 1 and Group 2-Session 1 in column C1 and for Group 1 and Group 2-Session 2 in column C2.

With a P-Value of $0.000^1$ at $\alpha(0.05)$, the research rejects the null. Thus, the alternative hypothesis that the PERC System improved event utilization efficiency observations is supported. Since this data set was not normally distributed at $\alpha(0.1)$, A Wilcoxon test was used with the first set of observations used (Event utilization Efficiency). FIG. 38 displays the test results and the data for Group 1 and Group 2-Session 1 in column C1 and for Group 1 and Group 2-Session 2 in column C2.

With a P-Value of 0.036 at $\alpha(0.1)$, the research rejects the null. Thus, the alternative hypothesis that the PERC System improved Event Utilization observations is supported.

FIGS. 35-37 and 39 show results for the prototype testing.

TABLE 5-18

Event Utilization Hypothesis Results $U_{v_1}$ - Event utilization parameter (Session 1)   $U_{v_2}$ - Event utilization parameter (Session 2)
$H_0$ = PERCS had no significant effect on event utilization observations $U_{v_2} = U_{v_1}$
$H_1$= PERCS improved event utilization observations $U_{v_2} > U_{v_1}$ Summary of Statistical Analysis Results The following table provides a summary of the results for the statistical tests used for the proof of concept.

Summary of Statistical Analysis

| Data Element | Design/ Prototype | Test Used | Results |
| --- | --- | --- | --- |
| Time Parameter - Second Session 2 ($t_{\alpha_p}$). | Design | T-Test | Unable to Reject the Null Hypothesis |
| | | Mann-Whitney | Unable to Reject the Null Hypothesis |
| Event Utilization - Second Session ($U_{v_2}$) | Design | T-Test | Unable to Reject the Null Hypothesis |
| | | Mann-Whitney | Unable to Reject the Null Hypothesis |

Summary of Statistical Analysis

| Data Element | Design/Prototype | Test Used | Results |
|---|---|---|---|
| Event Utilization - All Observations ($U_{v_1}$ & $U_{v_2}$) Patient Files | Design | General Linear Model | No Association Unable to Reject the Null Hypothesis |
| Event Utilization - All Observations ($U_{v_1}$ & $U_{v_2}$) Group Assignment | Design | General Linear Model | No Association Unable to Reject the Null Hypothesis |
| Time Parameter - Group 1 and Group 2 ($t_\alpha$ & $t_{\alpha_p}$) | Prototype | T-Test | Reject the Null Hypothesis |
| | | Wilcoxon | Reject the Null Hypothesis |
| Transportation Efficiency Group 1 and Group 2 ($U_{k_1}$ & $U_{k_2}$) | Prototype | T-Test | Reject the Null Hypothesis |
| | | Wilcoxon | Reject the Null Hypothesis |
| Destination Efficiency Group 1 and Group 2 ($U_{d1}$ & $U_{d2}$) | Prototype | Wilcoxon | Reject the Null Hypothesis |
| Patient Safe - Group 1 and Group 2 ($PS_1$ & $PS_2$) | Prototype | Wilcoxon | Reject the Null Hypothesis |
| Event Utilization Parameter Group 1 and Group 2 ($U_{v1}$ & $U_{v2}$) | Prototype | T-Test | Reject the Null Hypothesis |
| | | Wilcoxon | Reject the Null Hypothesis |

This disclosure began with an in-depth analysis of how hospital evacuations are conducted and how scholastic review of these evolutions attempted to define and represent them. The area of study was so recently developed that early researchers set aside the more involved variables in order to establish the framework for an overall evacuation event. Given the multiple disciplines involved, these researchers acknowledged that to define complex patient variables would be difficult and require a multifaceted approach.

One of the complex variables set aside represented the patient cohort, which included the challenges of either determining what broad categories could be created to effectively define this variable or to find a way to incorporate the individual issues of each patient into the overall process (Childers, Visagamurthy, & Taaffe, 2009) (Bish, Agca, & Glick, 2011). This dissertation research undertook the task to address this patient/patient cohort variable. The initiative was developed in five separate phases, which included the use of engineered functional decomposition and requirements analysis, model and simulation assessment, identifying specific concepts within separate medical professional protocols, creating a method to identify relationships between these concepts, creating a prototype to test the method developed, and then testing the prototype with a panel of healthcare professionals. The result of these efforts is the Patient Evacuation Resource Classification System (PERCS), a decision support tool that employs the research findings to provide guidance during emergency hospital evacuations.

This effort produced a Patient Evacuation Resource Classification System (PERCS) comprised of new classification terms and a series of sub models that identify the most appropriate transportation and destination resources the patient requires for a safe evacuation while minimizing the expenditure of excess resource capabilities applied to each patient movement. The research introduces an efficiency concept and matching protocols with a software application programming interface (API) with supporting algorithms that enables the system to expedite the identification of a transportation resource's specific capabilities and of the continued care capacities of predetermined destination facilities. The system also provides methodology to determine if a specific patient should be accompanied by staff or special equipment/medicines that supplement existing destination and transportation options to achieve a patient safe evacuation. PERCS is designed as a decision support tool providing visibility on multiple resource choices, displaying their capacity to safely meet the patient's resource needs plus an efficiency score for each to suggest the best match. The system also provides visibility on the patient cohort evacuation process allowing decision-makers to determine how best to use the limited availability of high value resources with robust capabilities such as a scarce Intensive Care Unit (ICU) or a Pediatric Critical Care Truck.

The PERC System is capable of scaling recommendations based on the nature of the environment and can adjust as the situation changes. During controlled disasters or events where primary communication and data connections are intact, as well as, infrastructure is stable and response capabilities are robust, the PERC System can be set to limit user choices to only Patient Safe (GREEN) options. However, during disasters where resources that offer usual standards of care are scarce or limited, the PERC System can be adjusted to allow users to choose Patient Safe or Potential Patient Safe resources (without upgrades) to provide the best possible care given the circumstances. Finally, in the event of a catastrophic event, the PERC System would be adjusted to allow the user to choose any available resource under the premise that the patient's safety is at greater risk remaining at the facility than being transported by any available means, and/or being transported to any other location regardless of continued care capabilities.

To ensure that no one receiving facility is overwhelmed with multiple critical care or complex care patients, the PERC System is capable of temporarily removing a facility from any immediate consideration after being assigned a critical care or complex care patient. The facility would still be displayed as a destination option if the follow-on patients are stable or non-critical care. The temporary omission protocol can be determined by multiple criteria; but the primary two would either recognize the admission of the initial critical care or complex care patient to the new destination OR work from a transport timeline allowing for another critical care or complex care patient to be assigned based on estimations that the original patient will be cleared from the destination hospital's admissions area. This feature can be adapted if a destination facility can support more than one critical care or complex care patient.

During the PERC System deployment for a client healthcare coalition, core transportation resources are evaluated and entered into the coalition PERC database for quick reference, however, changes in personnel assignments and/or equipment damage or failure may require live database intervention to properly display that resource's PERC capabilities at that very moment. Live database intervention may also be required if out of area resources arrive (that have not been evaluated prior to staging) to support the evacuation. The EMS PERC manager at the staging area would be able to edit or enter resources as required.

Incorporation Into Existing Protocols

According to at least one computer hardware and software-based technological embodiment of the disclosure, the PERCS may invoke a software application programming interface (API) to have functionality to electronically translate a patients electronic health record (EHR) into a standardized PERC patient profile. Software that can rapidly search a patients EHR to identify designated health resources currently in use by the patient can therefore be a relatively straightforward matching program, rather than having to interpret diagnoses and conditions and guess at patient resource requirements, or ask the patients nurse or medical provider a long list of questions. These efforts could benefit from incorporating the electronic bed board interface from those hospitals who use this system, further minimizing any separate user input requirements for the PERC System. Under ideal conditions, the PERC System would operate as a background tool capitalizing on existing data entry requirements.

In contrast, the PERC profile for each transportation vehicle in an EMS fleet can be developed during preparedness activities and retained in a database available for emergencies. The PERC profile for destination facilities is similarly straightforward, since the required resources are similar to or identical to those used by the patient at the evacuating facility. Setting up a database that can rapidly access transport vehicles PERC profile, ideally through a bar scanning system as the vehicle arrives in staging, would be another step in the PERC System implementation.

PERC System Assessment Capabilities

The PERC System could be used to assess a city or region's residential healthcare facilities to objectively determine the resource requirements to evacuate one, multiple, or all facilities. Each evacuation scenario assessed to identify and aggregate the transportation and destination resources (including flex resources from evacuating and assisting facilities) that would be required in the event of a major emergency (massive flooding or earthquake, nuclear fallout, etc.).

The six assumptions for adequate implementation may include:

1) Integration into each electronic health record (EHR) system. This capability is easily accomplished using software recognition to find resources in the EHR);

2) Standardized assessment of EMS and other transport resources that would be used in the evacuation (e.g., resource description using PERC terms tied to bar code on the vehicle so it can be scanned as it arrives in vehicle staging and information is transmitted electronically to PERC software tool used by decision-maker);

3) Integration into existing census reporting for healthcare facilities within a coalition. Standardized assessment of each bed space (e.g., resource description using PERC terms by room/bed code). Empty or unassigned beds would be reflected in PERCS as "bed availability" so it is consistent with and live feeds into the PERC software tool;

4) Integration into existing staffing and supply systems. This capability is easily accomplished using software recognition to find resources and translate them into PERC profiles.

5) Training will be available (and accessed) for hospital & EMS decision-makers, for coalition personnel who would assist an evacuating healthcare facility, and for those funding the implementation of the PERC system;

6) Healthcare facility decision-makers will trust and use the PERC decision-support tool.

Although the invention has been defined using the appended claims, these claims are exemplary in that the invention may be intended to include the elements and steps described herein in any combination or sub combination. Accordingly, there are any number of alternative combinations for defining the invention, which incorporate one or more elements from the specification, including the description, claims, and drawings, in various combinations or sub combinations.

According to one aspect of the disclosure, methods are contemplated to read/analyze patient EHRs to produce a patient PERC profile. The software-generated patient PERC profiles are contemplated to accurately represent the patient's resource needs based on their current medical condition. For example, an extension of the current PERC patient profiles could be amended to include new or experimental equipment, including unusual and highly sophisticated equipment such as Extracorporeal Membrane Oxygenation (ECMO). The PERC System 100 can provide information recommendation to include specialized staff support and ancillary equipment when a complex resource is identified. For example, a ventilator resource requirement includes all of the various supplies and the intervention medical skill sets necessary to properly use this equipment.

It is contemplated within the scope of the disclosure that PERCS interface features could be developed and assessment protocols could incorporate multiple transportation resources (multi-modal) options to include air, sea, and even rail resources; PERCS interface features may include the use of transfer stations potentially required by resource range constraints or infrastructure limitations (multi-nodal), and/or incorporating both (multi-modal and multi-nodal). It is contemplated that PERC guidelines for testing under multiple conditions that range from that in the current study (emergency evacuation but with time and resources for "safe" patient transport) to decision support in extreme emergencies when patients may be matched to "as safe as available under the circumstances" resources. Military units and foreign aid assets should also be assessed to address language, culture, and terminology challenges. Finally, later developed technologies could be considered within the PERCS system, as applicable, such as artificial intelligent systems, including self-driving resources.

It will be apparent to those skilled in the relevant technology, in light of the present specification, that alternate combinations of aspects of the invention, either alone or in combination with one or more elements or steps defined herein, may be utilized as modifications or alterations of the invention or as part of the invention. It may be intended that the written description of the invention contained herein covers all such modifications and alterations.

What is claimed is:

1. An automated decision support computer system based on processing of data informatics, comprising:
a processor, a dynamic database, and a computer screen display;
the processor being configured to receive a plurality of computer readable data packets from at least one computer data network;
a first computer readable processing module operable with the processor for electronically processing a plurality of dynamic destination resource attribute data packets and dynamic transportation resource attribute data packets; the dynamic destination resource attribute data packets and the dynamic transportation resource attribute data packets being at least partially generated from a first application programming interface having a computer protocol associated with a plurality of electronic computer readable geo-location destination data;
a second computer readable processing module operable with the processor for electronically processing a plurality of dynamic patient classification attribute data packets; the dynamic patient classification attribute data packets being at least generated from a second application programming interface having a computer datamining protocol for a plurality of dynamic computer readable electronic health records; and a decision support classification computer engine operable with the processor for electronically processing a scoring and ranking engine including dichotomous attribute data processing of the plurality of dynamic destination resource attribute data packets and the dynamic transportation resource attribute data packets with the plurality of dynamic patient classification attribute data packets for generating a plurality of computer readable evacuation attribute data profiles associated with the dynamic computer readable electronic health records and for storing the plurality of computer readable evacuation attribute data profiles in the dynamic database to display on a graphical user interface of the computer screen display;

wherein the scoring and ranking engine is configured for dichotomous attribute data processing of at least a first sum of matches between the plurality of dynamic transportation resource attribute data packets associated with the plurality of dynamic patient classification attribute data packets, said first sum being defined by $\Sigma_i f_i(x, t)$ wherein i being associated with match pairs, x being associated with the plurality of dynamic patient classification attribute data packets, and t being associated with the plurality of dynamic transportation resource attribute data packets;

wherein the scoring and ranking engine is configured for dichotomous attribute data processing of at least a second sum of matches between the plurality of dynamic destination resource attribute data packets associated with the plurality of dynamic patient classification attribute data packets, said second sum being defined by $\Sigma 1 f_i(x,d)$ wherein i being associated with said match pairs, x being associated with the plurality of dynamic patient classification attribute data packets, and d being associated with the plurality of dynamic destination resource attribute data packets;

wherein the scoring and ranking engine is configured for dichotomous attribute data processing of at least a third sum of associated with the plurality of dynamic patient classification attribute data packets, said third sum being defined by $\Sigma_i(x)$ wherein i being associated with said match pairs, x being associated with the plurality of dynamic patient classification attribute data packets;

wherein the scoring and ranking engine is configured to generate a computer readable transportation safety score based on a ratio of the first sum and the third sum; the scoring and ranking engine being configured to compare the transportation safety score to a threshold value and if not a match, the engine being configured to electronically select at least one computer readable flex resource attribute data element for least one of the computer readable evacuation attribute data profiles;

wherein the scoring and ranking engine is configured to generate a computer readable destination safety score based on a ratio of the second sum and the third sum.

2. The automated decision support computer system according to claim 1, wherein the decision support classification computer engine includes a first computer readable efficiency component associated with the destination safety score and a second computer readable efficiency component associated with transportation safety score for said scoring and ranking engine.

3. The automated decision support computer system according to claim 1, wherein the computer readable evacuation attribute data profiles includes at least one patient-safe attribute transportation data element further comprising the graphical user interface configured for displaying the at least one patient-safe attribute transportation data element different from other computer readable evacuation attribute data profiles.

4. The automated decision support computer system according to claim 1, wherein the computer readable evacuation attribute data profiles includes at least one patient-safe attribute destination resource data element and further comprising the graphical user interface configured for displaying the at least one patient-safe destination resource data element different from other computer readable evacuation attribute data profiles.

5. The automated decision support computer system of claim 1, wherein the scoring and ranking engine being configured to compare the destination safety score to a threshold value and if not a match, electronically selecting at least one computer readable flex destination resource attribute data element for least one of the computer readable evacuation attribute data profiles.

6. A computer implemented method for a decision support system based on health data informatics, the method comprising the steps of:

electronically processing a first computer readable database including a plurality of dynamic destination resource attribute data packets and a plurality of dynamic transportation resource attribute data packets; the dynamic destination resource attribute data packets and dynamic transportation resource attribute data packets being at least partially generated from a first application programming interface having a computer protocol associated with a plurality of electronic computer readable geo-location destination data;

electronically processing a second computer readable database including a plurality of dynamic patient classification attribute data packets; the dynamic patient classification attribute data packets being at least partially generated from a second application programming interface having a computer datamining protocol for a plurality of dynamic computer readable electronic health records;

processing on, a computer processor, a scoring and ranking engine including dichotomous attribute data processing of the plurality of dynamic destination resource attribute data packets and dynamic transportation resource attribute data packets with the plurality of dynamic patient classification attribute data packets for generating a plurality of computer readable evacuation attribute data profiles associated with the dynamic computer readable electronic health records; and displaying on a graphical user interface at least one of the computer readable evacuation attribute data profiles;

wherein the scoring and ranking engine is configured for dichotomous attribute data processing of at least a first sum of matches between the plurality of dynamic transportation resource attribute data packets associated with the plurality of dynamic patient classification attribute data packets, said sum being defined by $\Sigma_i f_i(x, t)$ wherein i being associated with match pairs, x being associated with the plurality of dynamic patient classification attribute data packets, and t being associated with the plurality of dynamic transportation resource attribute data packets;

wherein the scoring and ranking engine is configured for dichotomous attribute data processing of at least a second sum of matches between the plurality of dynamic destination resource attribute data packets associated with the plurality of dynamic patient classification attribute data packets, said second sum being defined by $\Sigma 1 f_i(x,d)$ wherein i being associated with said match pairs, x being associated with the plurality of dynamic patient classification attribute data packets, and d being associated with the plurality of dynamic destination resource attribute data packets;

wherein the scoring and ranking engine is configured for dichotomous attribute data processing of at least a third sum of associated with the plurality of dynamic patient classification attribute data packets, said third sum being defined by $\Sigma_i(x)$ wherein i being associated with said match pairs, x being associated with the plurality of dynamic patient classification attribute data packets;

wherein the scoring and ranking engine is configured to generate a computer readable transportation safety score based on a ratio of the first sum and the third sum; the scoring and ranking engine being configured to compare the transportation safety score to a threshold value and if not a match, the engine being configured to electronically select at least one computer readable flex resource attribute data element for least one of the computer readable evacuation attribute data profiles;

wherein the scoring and ranking engine is configured to generate a computer readable destination safety score based on a ratio of the second sum and the third sum.

7. The computer implemented method for a decision support system according to claim 6, wherein the scoring and ranking engine includes a first computer readable efficiency component associated with the destination safety score and a second computer readable efficiency component associated with the transportation safety score.

8. The computer implemented method for a decision support system according to claim 6, wherein the computer readable evacuation attribute data profiles includes at least one patient-safe attribute transportation data element and further comprising modifying the graphical user interface for displaying the at least one patient-safe attribute transportation data element different from other computer readable evacuation attribute data profiles.

9. The computer implemented method for a decision support system according to claim 6, wherein the computer readable evacuation attribute data profiles includes at least one patient-safe attribute destination resource data element and further comprising modifying the graphical user interface for displaying the at least one patient-safe attribute destination resource data element different from other computer readable evacuation attribute data profiles.

10. The method of claim 6, wherein the scoring and ranking engine being configured to compare the destination safety score to a threshold value and if not a match, electronically selecting at least one computer readable flex destination resource data element for least one of the computer readable evacuation attribute data profiles.

11. A computer implemented method for a decision support system based on health data informatics, the method comprising the steps of:

electronically processing a plurality of dynamic destination resource attribute data packets and a plurality of dynamic transportation resource attribute data packets being generated from a first application programming interface having a computer protocol associated with a plurality of electronic computer readable GPS-location destination data;

electronically processing a plurality of dynamic patient classification attribute data packets; the plurality of dynamic patient classification attribute data packets being generated from a plurality of dynamic computer readable electronic health records;

electronically transmitting the plurality of dynamic destination resource attribute data packets, the plurality of dynamic transportation resource attribute data packets and the plurality of dynamic patient classification attribute data packets in a cloud computer network to a scoring and ranking engine; determining if there is a network transmission failure in the cloud computer network, and responsive thereto, transmitting the plurality of dynamic destination resource attribute data packets, the plurality of dynamic transportation resource attribute data packets and the plurality of dynamic patient classification attribute data packets to the scoring and ranking engine via a cell-on-wheels mobile data transmission apparatus;

processing on, a computer processor, the scoring and ranking engine including dichotomous attribute data processing of the plurality of dynamic destination resource attribute data packets and the plurality of dynamic transportation resource attribute data packets with the plurality of dynamic patient classification attribute data packets to generate a plurality of computer readable evacuation attribute data profiles associated with the dynamic computer readable electronic health records; and displaying on a computer graphical user interface at least one of the computer readable evacuation attribute data profiles;

wherein the scoring and ranking engine is configured for dichotomous attribute data processing of at least a sum of matches between the plurality of dynamic transportation resource attribute data packets associated with the plurality of dynamic patient classification attribute data packets, said sum being defined by $\Sigma_i f_i(x, t)$ wherein i being associated with match pairs, x being associated with the plurality of dynamic patient classification attribute data packets, and t being associated with the plurality of dynamic transportation resource attribute data packets;

wherein the scoring and ranking engine is configured for dichotomous attribute data processing of at least a second sum of matches between the plurality of dynamic destination resource attribute data packets associated with the plurality of dynamic patient classification attribute data packets, said second sum being defined by $\Sigma 1 f_i(x,d)$ wherein i being associated with said match pairs, x being associated with the plurality of dynamic patient classification attribute data packets, and d being associated with the plurality of dynamic destination resource attribute data packets;

wherein the scoring and ranking engine is configured for dichotomous attribute data processing of at least a third sum of associated with the plurality of dynamic patient classification attribute data packets, said third sum being defined by $\Sigma_i(x)$ wherein i being associated with said match pairs, x being associated with the plurality of dynamic patient classification attribute data packets;

wherein the scoring and ranking engine is configured to generate a computer readable transportation safety score based on a ratio of the first sum and the third sum; and wherein the scoring and ranking engine is configured to generate a computer readable destination safety score based on a ratio of the second sum and the third sum.

12. The computer implemented method for a decision support system according to claim 11, wherein the scoring and ranking engine being configured to compare the transportation safety score to a threshold value and if not a match, the engine being configured to electronically select at least one computer readable flex resource attribute data element for least one of the computer readable evacuation attribute data profiles.

13. The computer implemented method for a decision support system according to claim 11, wherein at least one of the computer readable evacuation attribute data profiles includes at least one patient-safe attribute destination resource data element.

14. The computer implemented method for a decision support system according to claim 11, wherein the plurality of dynamic patient classification attribute data packets includes a ventilation attribute data element.

15. The computer implemented method for a decision support system according to claim 11, wherein the plurality of dynamic patient classification attribute data packets includes a cardiovascular attribute data element.

* * * * *